US005407823A

United States Patent [19]

Sokoloff et al.

[11] Patent Number: 5,407,823

[45] Date of Patent: Apr. 18, 1995

[54] POLYPEPTIDES HAVING A DOPAMINERGIC RECEPTOR ACTIVITY, NUCLEIC ACIDS CODING FOR THESE POLYPEPTIDES AND USE OF THESE POLYPEPTIDES FOR THE SCREENING OF SUBSTANCES ACTIVE ON THESE POLYPEPTIDES

[75] Inventors: Pierre Sokoloff, Le Plessis Bouchard; Marie-Pascale Martres; Jean-Charles Schwartz, both of Paris; Giros Bruno, Chatillon, all of France

[73] Assignee: Institut National de la Sante et de la Recherche Medicale, Paris, France

[21] Appl. No.: 781,254

[22] PCT Filed: Apr. 3, 1991

[86] PCT No.: PCT/FR91/00269

§ 371 Date: Dec. 31, 1991

§ 102(e) Date: Dec. 31, 1991

[87] PCT Pub. No.: WO91/15513

PCT Pub. Date: Oct. 17, 1991

[30] Foreign Application Priority Data

Apr. 6, 1990 [FR] France ................................ 90 04476
Jun. 26, 1990 [FR] France ................................ 90 08027

[51] Int. Cl.$^6$ ........................ C07K 13/00; C12N 15/12

[52] U.S. Cl. .............................. 435/252.3; 435/320.1; 530/350; 536/23.5

[58] Field of Search ................. 435/69.1, 252.3, 370.1; 530/350; 536/27

[56] References Cited

U.S. PATENT DOCUMENTS 4,675,285 6/1987 Clark et al. ............................ 435/6

OTHER PUBLICATIONS

Biochem. Pharmacol. 31; 1183-1187, 1982, Davis et al. Solubilized Receptors for [$^3$H] dopamine ($D_3$ Binding Sites) From Canine Brain.

Nature 329; 836-838, 29 Oct. 1987, Masu et al. cDNA cloning of bovine substance-K receptor through oocyte expression system.

Harlow and Lane, *Antibodies: A Laboratory Manual,* Cold Spring Harbor Laboratory, publisher; Cold Spring Harbor, N.Y.; Contents pp. iii-ix (1988).

Martes et al., "Widespread Distribution of Brain Dopamine Receptors Evidenced with [$^{125}$I]Iodosulpride, a Highly Selective Ligand", *Science,* 228:752-755 (1985).

Sokoloff et al., "Three classes of Dopamine Receptor (D-2, D-3, D-4) Identified by Binding Studies with $^3$H-Apomorphine and $^3$H-Doperidone", *Naunyn-Smiedebergs Arch. Pharmacol.,* 315:89-102 (1980).

*Primary Examiner*—Robert J. Hill, Jr.
*Assistant Examiner*—John D. Ulm
*Attorney, Agent, or Firm*—Merchant, Gould, Smith, Edell, Welter & Schmidt

[57] ABSTRACT

The invention is directed to novel polypeptides having dopaminergic receptor activity and nucleic acid sequences encoding these novel polypeptides. The novel polypeptides are useful as drugs and/or to screen other drugs that affect dopaminergic receptors. The nucleic acid sequences are useful as diagnostic agents and to prepare transformed cells and vectors expressing the novel polypeptides.

12 Claims, 21 Drawing Sheets

FIG. 1A

```
1        10         20          30       40       50       60
MAPLS-Q-ISTHLNSTCG-AENSTGVN-RA-RPH-AYYALSYCALILAIIFGNGLVCAAVLRERALQTTT
MDPLNLSWYDDDLERQ-NWSRPFNGSEGKADRPHYNYYAMLLTLLIFIIVFGNVLVCMAVSREKALQTTT
1        10        20        30        40        50        60

  70        80        90       100       110       120       130
NYLVVSLAVADLLVATLVMPWVVYLEVTGGVWNFSRICCDVFVTLDVMMCTASILNLCAISIDRYTAVVM
NYLIVSLAVADLLVATLVMPWVVYLEVVGE-WKFSRIHCDIFVTLDVMMCTASILNLCAISIDRYTAVAM
        80        90       100       110       120       130

  140       150       160       170       180       190       200
PVHYEHGTGQSSCRRVALMITAVWVLAFAVSCPLLFGFNTTGDPSICSISNPDFVIYSSVVSFYVPFGVT
PMLYNTRYS-SK-RRVTVMIAIVWVLSFTISCPLLFGLNNT-DQNECIIANPAFVVYSSIVSFYVPFIVT
            150       160       170       180       190       200

  210       220       230       240       250       260       270
VLVYARIYIVLRQRQRKRILTRQNSQCISIRPGF--PQQSSCLRLHPIRQFSIRARFLSDATG-QMEHIE
LLVYIKIYIVLRKR-RKRVNTKRSSR--AFRANLKTPLKGNC-T-HP-EDMKLCTVIMKSNGSFPVNR-R
  210       220       230       240       250       260
```

Figure 1B:
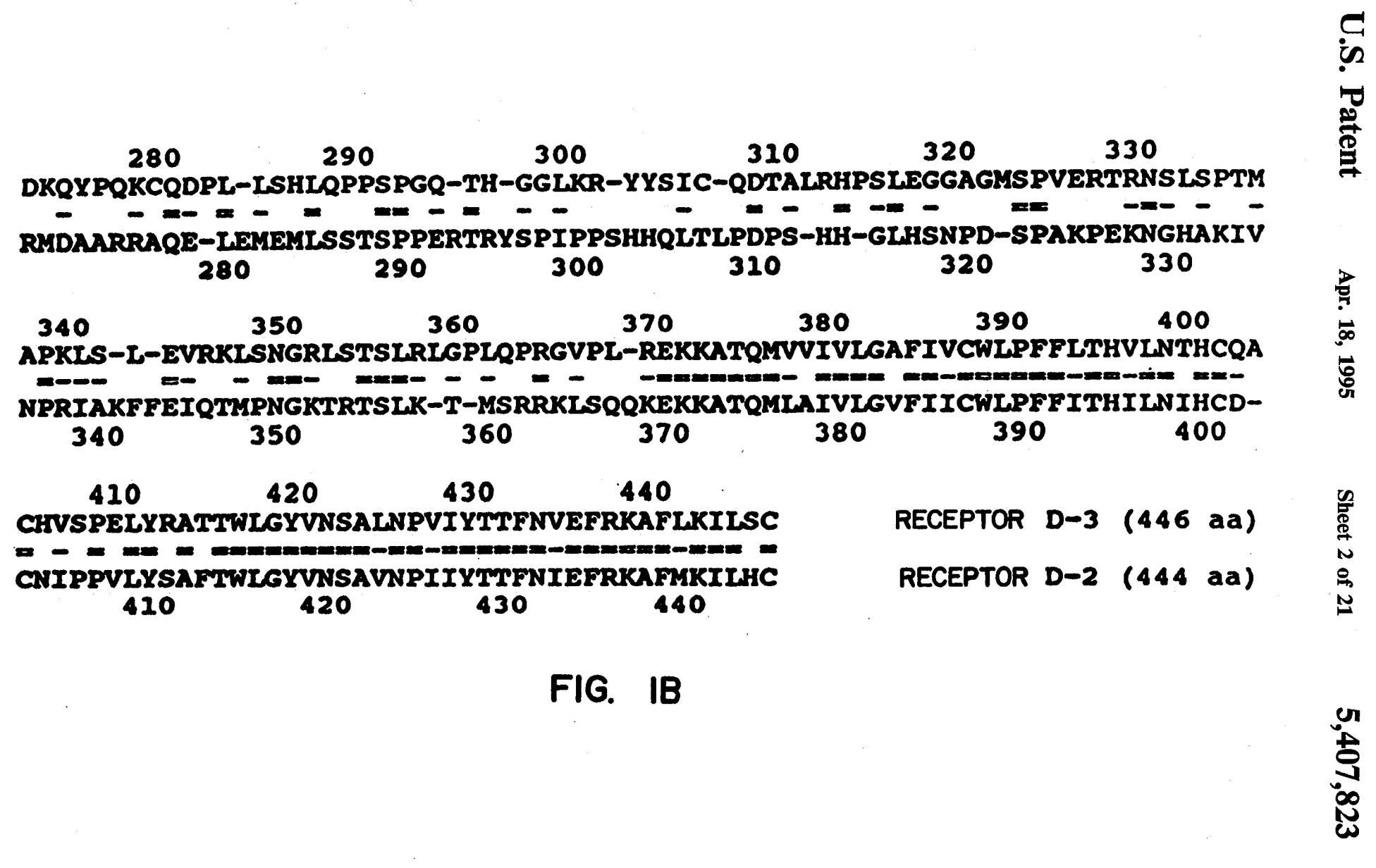

```
   280        290         300         310        320        330
DKQYPQKCQDPL-LSHLQPPSPGQ-TH-GGLKR-YYSIC-QDTALRHPSLEGGAGMSPVERTRNSLSPTM

RMDAARRAQE-LEMEMLSSTSPPERTRYSPIPPSHHQLTLPDPS-HH-GLHSNPD-SPAKPEKNGHAKIV
       280        290        300       310         320        330

340         350        360        370        380        390        400
APKLS-L-EVRKLSNGRLSTSLRLGPLQPRGVPL-REKKATQMVVIVLGAFIVCWLPFFLTHVLNTHCQA

NPRIAKFFEIQTMPNGKTRTSLK-T-MSRRKLSQQKEKKATQMLAIVLGVFIICWLPFFITHILNIHCD-
  340        350         360        370        380        390        400

  410        420        430        440
CHVSPELYRATTWLGYVNSALNPVIYTTFNVEFRKAFLKILSC      RECEPTOR D-3 (446 aa)

CNIPPVLYSAFTWLGYVNSAVNPIIYTTFNIEFRKAFMKILHC      RECEPTOR D-2 (444 aa)
    410        420        430        440
```

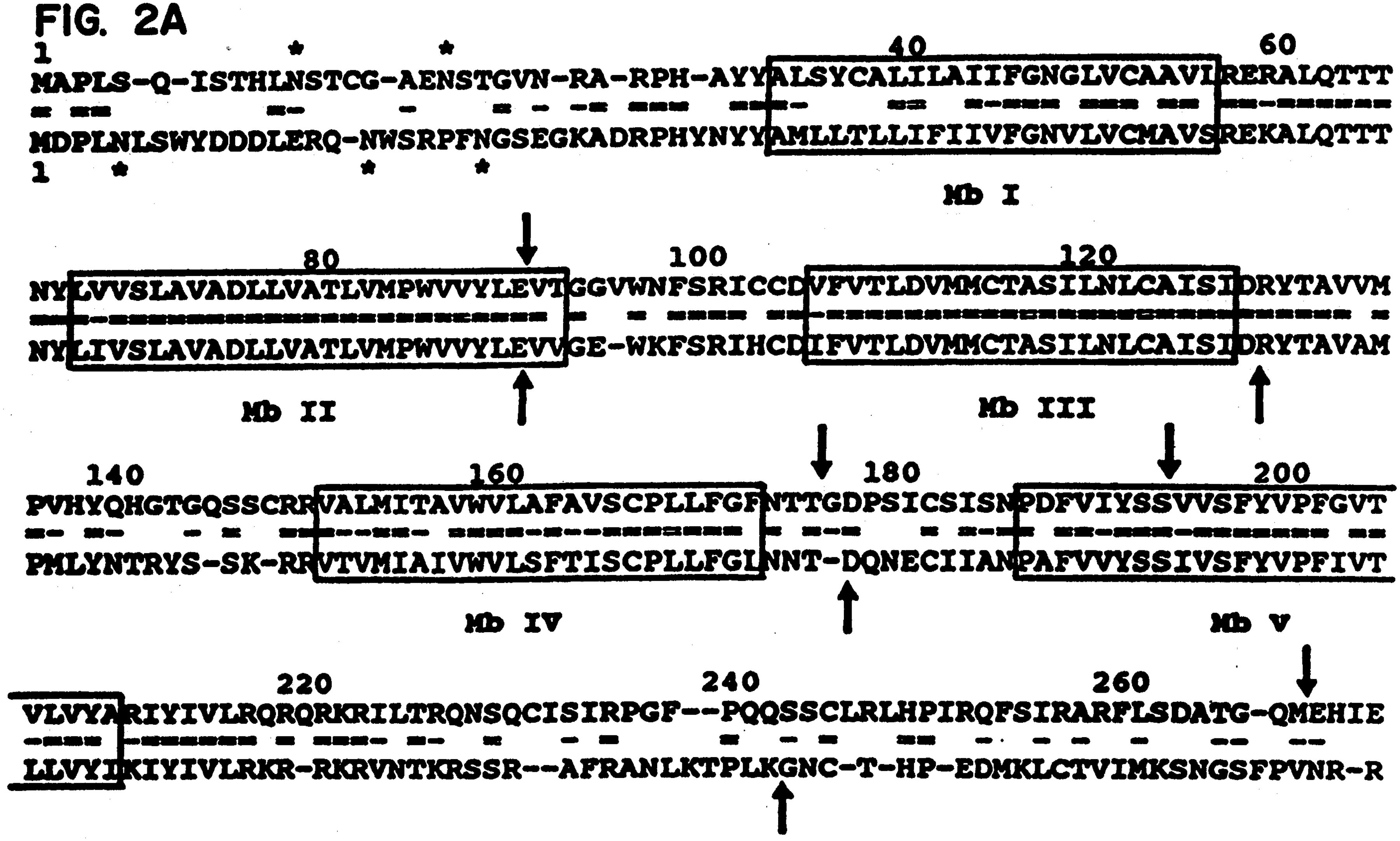

```
1                                                                                60
MAPLS-Q-ISTHLNSTCG-AENSTGVN-RA-RPH-AYYALSYCALILAIIFGNGLVCAAVLRERALQTTT
 --  - ---------  ------- -- --- ---------------------------------
MDPLNLSWYDDDLERQ-NWSRPFNGSEGKADRPHYNYYAMLLTLLIFIIVFGNVLVCMAVSREKALQTTT
1         *                 *              Mb I

                                                                               120
NYLVVSLAVADLIVATLVMPWVVYLEVTGGVWNFSRICCDVFVTLDVMCTASILNLCAISIDRYTAVVM
-- ------------------------ -- ---------------------------------
NYLIVSLAVADLIVATLVMPWVVYLEVVGE-WKFSRIHCDIFVTLDVMCTASILNLCAISIDRYTAVAM
         Mb II                              Mb III

                                                                               200
PVHYQHGTGQSSCRFVALMITAVWVLAFAVSCPLLFGNTTGDPSICSISNPDFVIYSSVVSFYVPFGVT
-------- --- ----------------------- -------- --------------------
PMLYNTRYS-SK-RRVTVMIAIVWVLSFTISCPLLFGINNT-DQNECIIANPAFVVYSSIVSFYVPFIVT
              Mb IV                              Mb V

                                                                               260
VLVYARIYIVLRQRQRKRILTRQNSQCISIRPGF--PQQSSCLRLHPIRQFSIRARFPLSDATG-QMEHIE
------- ----------------------- ---------------------------- --
LLVYIKIYIVLRKR-RQRVNTKRSSR--AFRANLKTPLKGNC-T-HP-EDMKLCTVIMKSNGSFPVNR-R
        220                    240
```

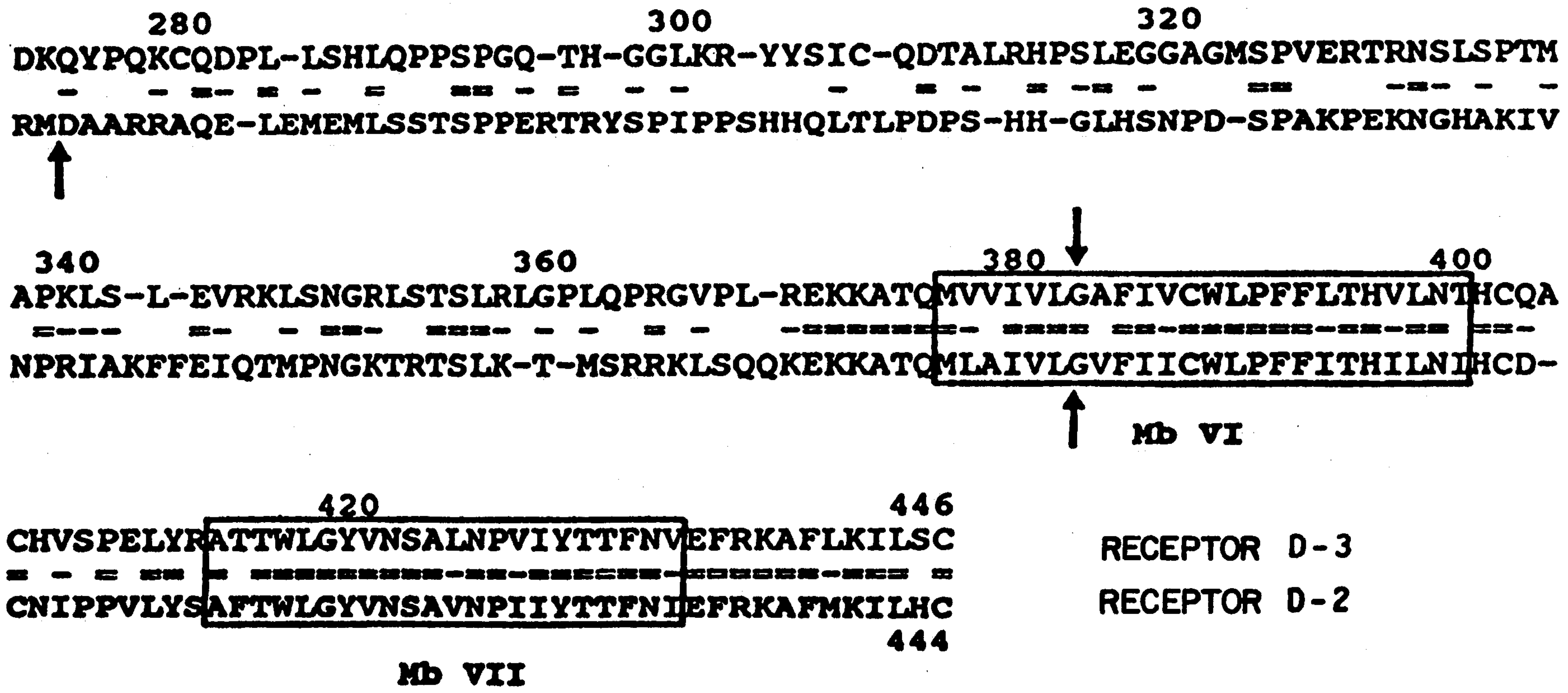

FIG. 2B

```
                280                  300                  320
DKQYPQKCQDPL-LSHLQPPSPGQ-TH-GGLKR-YYSIC-QDTALRHPSLEGGAGMSPVERTRNSLSPTM
  -  - = -  =  ==  =  =                   -              ==  =   -

RMDAARRAQE-LEMEMLSSTSPPERTRYSPIPPSHHQLTLPDPS-HH-GLHSNPD-SPAKPEKNGHAKIV

                340                  360                  380                400
APKLS-L-EVRKLSNGRLSTSLRLGPLQPRGVPL-REKKATQ|VVIVLGAFIVCWLPFFLTHVLNT|HCQA
====  -  - =  -  == ===  -   - -                ==  --- == =       -  ---
NPRIAKFFEIQTMPNGKTRTSLK-T-MSRRKLSQQKEKKATQ|MLAIVLGVFIICWLPFFITHILN|HCD-
                                                    ↑  MbVI  ↑

                                                          RECEPTOR D-3
                                                          RECEPTOR D-2

                420                                       446
CHVSPELYR|ATTWLGYVNSALNPVIYTTFNV|EFRKAFLKILSC
 = -  =  ==                          ===---
CNIPPVLYSA|FTWLGYVNSAVNPIIYTTFNI|EFRKAFMKILHC
                                                          444
          MbVII
```

FIG. 3A

```
gctagccttgccttcactgctaatatagccaggaagccttcttgttatctaa     52
tatagccaggaagccttcttgttatctaactgtgcttacccacaatcatacc    104
atcctcgaccactccccaactcccatttctgatttacttttctccaaaaagc    156
ataatatcgcagaacaggtcttatcttgattataaatcttctcccccccccc    208
caaccccatagaggtttcataagggaagaaatgtctgttcctttcctaactg    260
tatttctggttctatagcactgcctgctctatatagaaatgttccatcgata    312
tttgtagacatgaaacattttaaactgtatgtatgtaacatatcccagctct    364
gaagagcctgatttagcccacattgctgtctgtcttttcctaggaacatttt    416

ggagtcgcgttcctctgtgtgggcc ATG GCA CCT CTG AGC CAG       459
                          Met Ala Pro Leu Ser Gln         6

ATA AGC ACC CAC CTC AAC TCC ACC TGC GGG GCA GAA AAC     498
Ile Ser Thr His Leu Asn Ser Thr Cys Gly Ala Glu Asn      19

TCC ACT GGC GTC AAC CGG GCC CGT CCG CAC GCC TAC TAC     537
Ser Thr Gly Val Asn Arg Ala Arg Pro His Ala Tyr Tyr      32

GCC CTG TCC TAC TGT GCT CTC ATC CTA GCC ATC ATC TTT     576
Ala Leu Ser Tyr Cys Ala Leu Ile Leu Ala Ile Ile Phe      45

GGC AAC GGC CTG GTA TGT GCT GCT GTG CTG AGG GAG CGT     615
Gly Asn Gly Leu Val Cys Ala Ala Val Leu Arg Glu Arg      58

GCC CTG CAG ACC ACC ACC AAC TAC CTA GTG GTG AGC CTG     654
Ala Leu Gln Thr Thr Thr Asn Tyr Leu Val Val Ser Leu      71

GCT GTG GCC GAC CTG CTA GTG GCC ACG TTG GTG ATG CCG     693
Ala Val Ala Asp Leu Leu Val Ala Thr Leu Val Met Pro      84
```

FIG. 3B

TGG GTG GTG TAC TTG GAG GTG ACA GGT GGA GTC TGG AAT 732
Trp Val Val Tyr Leu Glu Val Thr Gly Gly Val Trp Asn 97

TTC AGC CGC ATT TGC TGT GAC GTT TTT GTC ACC CTG GAT 771
Phe Ser Arg Ile Cys Cys Asp Val Phe Val Thr Leu Asp 110

GTC ATG ATG TGT ACA GCC AGC ATC CTG AAC CTC TGT GCC 810
Val Met Met Cys Thr Ala Ser Ile Leu Asn Leu Cys Ala 123

ATC AGC ATA GAC AGG TAC ACA GCG GTG GTC ATG CCA GTT 849
Ile Ser Ile Asp Arg Tyr Thr Ala Val Val Met Pro Val 136

CAC TAT GAG CAC GGC ACC GGG CAG AGC TCC TGT AGA CGT 888
His Tyr Glu His Gly Thr Gly Gln Ser Ser Cys Arg Arg 149

GTG GCA CTC ATG ATC ACA GCT GTG TGG GTG CTG GCT TTT 927
Val Ala Leu Met Ile Thr Ala Val Trp Val Leu Ala Phe 162

GCT GTG TCC TGC CCT CTC CTC TTT GGT TTC AAC ACA ACA 966
Ala Val Ser Cys Pro Leu Leu Phe Gly Phe Asn Thr Thr 175

GGG GAT CCC AGC ATC TGC TCC ATC TCC AAC CCT GAT TTT 1005
Gly Asp Pro Ser Ile Cys Ser Ile Ser Asn Pro Asp Phe 188

GTC ATT TAC TCT TCA GTG GTG TCC TTC TAC GTT CCC TTC 1044
Val Ile Tyr Ser Ser Val Val Ser Phe Tyr Val Pro Phe 201

FIG. 3C

```
GGG GTG ACT GTC CTG GTC TAT GCC AGG ATC TAC ATA GTC  1083
Gly Val Thr Val Leu Val Tyr Ala Arg Ile Tyr Ile Val   214

CTG AGG CAA AGG CAA AGA AAA CGG ATC CTC ACT CGA CAG  1122
Leu Arg Gln Arg Gln Arg Lys Arg Ile Leu Thr Arg Gln   227

AAC AGC CAG TGC ATC AGT ATC AGA CCT GGC TTT CCT CAG  1161
Asn Ser Gln Cys Ile Ser Ile Arg Pro Gly Phe Pro Gln   240

CAG TCT TCC TGT CTG AGG CTG CAT CCC ATT CGG CAG TTT  1200
Gln Ser Ser Cys Leu Arg Leu His Pro Ile Arg Gln Phe   253

TCA ATA AGG GCC AGG TTT CTG TCA GAT GCC ACA GGA CAA  1239
Ser Ile Arg Ala Arg Phe Leu Ser Asp Ala Thr Gly Gln   266

ATG GAG CAC ATA GAA GAC AAA CAA TAT CCC CAG AAA TGC  1278
Met Glu His Ile Glu Asp Lys Gln Tyr Pro Gln Lys Cys   279

CAG GAC CCC CTT TTG TCA CAC CTG CAG CCC CCC TCA CCT  1317
Gln Asp Pro Leu Leu Ser His Leu Gln Pro Pro Ser Pro   292

GGT CAG ACA CAT GGG GGG CTG AAG CGC TAC TAC AGC ATC  1356
Gly Gln Thr His Gly Gly Leu Lys Arg Tyr Tyr Ser Ile   305

TGC CAA GAC ACT GCC TTG AGA CAC CCA AGC TTG GAA GGC  1395
Cys Gln Asp Thr Ala Leu Arg His Pro Ser Leu Glu Gly   318

GGG GCA GGG ATG AGC CCC GTG GAA AGG ACT CGG AAC TCC  1434
Gly Ala Gly Met Ser Pro Val Glu Arg Thr Arg Asn Ser   331
```

FIG. 3D

```
TTG AGC CCC ACC ATG GCA CCC AAG CTC AGC TTA GAG GTT   1473
Leu Ser Pro Thr Met Ala Pro Lys Leu Ser Leu Glu Val    344

CGA AAA CTC AGC AAC GGC AGG TTA TCC ACG TCC CTG AGG   1512
Arg Lys Leu Ser Asn Gly Arg Leu Ser Thr Ser Leu Arg    357

CTG GGG CCC CTG CAG CCT CGG GGA GTA CCA CTT CGA GAG   1551
Leu Gly Pro Leu Gln Pro Arg Gly Val Pro Leu Arg Glu    370

AAG AAG GCC ACC CAG ATG GTG GTC ATT GTG CTT GGA GCC   1590
Lys Lys Ala Thr Gln Met Val Val Ile Val Leu Gly Ala    383

TTC ATT GTC TGC TGG CTG CCC TTC TTC CTG ACT CAC GTT   1629
Phe Ile Val Cys Trp Leu Pro Phe Phe Leu Thr His Val    396

CTT AAT ACC CAC TGT CAA GCA TGC CAC GTG TCC CCA GAG   1668
Leu Asn Thr His Cys Gln Ala Cys His Val Ser Pro Glu    409

CTT TAC AGA GCC ACA ACG TGG CTA GGC TAT GTG AAC AGT   1707
Leu Tyr Arg Ala Thr Thr Trp Leu Gly Tyr Val Asn Ser    422

GCC CTG AAT CCT GTG ATC TAT ACC ACC TTC AAT GTG GAG   1746
Ala Leu Asn Pro Val Ile Tyr Thr Thr Phe Asn Val Glu    435

TTC CGC AAA GCC TTC CTC AAG ATC CTG TCC TGC tgaagga   1786
Phe Arg Lys Ala Phe Leu Lys Ile Leu Ser Cys            446

ggagaagagaccgcactccctttacccacttcgagatgccaggcagtttgaa  1838
ccctgcccatcagggtctggttggg                             1863
```

FIG. 4A

```
gctagccttgccttcactgctaatatagccaggaagccttcttgttatctaa   52
tatagccaggaagccttcttgttatctaactgtgcttacccacaatcatacc  104
atcctcgaccactccccaactcccatttctgatttacttttctccaaaaagc  156
ataatatcgcagaacaggtcttatcttgattataaatcttctcccccccccc  208
caaccccatagaggtttcataagggaagaaatgtctgttcctttcctaactg  260
tatttctggttctatagcactgcctgctctatatagaaatgttccatcgata  312
tttgtagacatgaaacattttaaactgtatgtatgtaacatatcccagctct  364
gaagagcctgatttagcccacattgctgtctgtcttttcctaggaacatttt  416

ggagtcgcgttcctctgtgtgggcc ATG GCA CCT CTG AGC CAG      459
                          Met Ala Pro Leu Ser Gln        6

ATA AGC ACC CAC CTC AAC TCC ACC TGC GGG GCA GAA AAC    498
Ile Ser Thr His Leu Asn Ser Thr Cys Gly Ala Glu Asn     19

TCC ACT GGC GTC AAC CGG GCC CGT CCG CAC GCC TAC TAC    537
Ser Thr Gly Val Asn Arg Ala Arg Pro His Ala Tyr Tyr     32

GCC CTG TCC TAC TGT GCT CTC ATC CTA GCC ATC ATC TTT    576
Ala Leu Ser Tyr Cys Ala Leu Ile Leu Ala Ile Ile Phe     45

GGC AAC GGC CTG GTA TGT GCT GCT GTG CTG AGG GAG CGT    615
Gly Asn Gly Leu Val Cys Ala Ala Val Leu Arg Glu Arg     58

GCC CTG CAG ACC ACC ACC AAC TAC CTA GTG GTG AGC CTG    654
Ala Leu Gln Thr Thr Thr Asn Tyr Leu Val Val Ser Leu     71
```

FIG. 4B

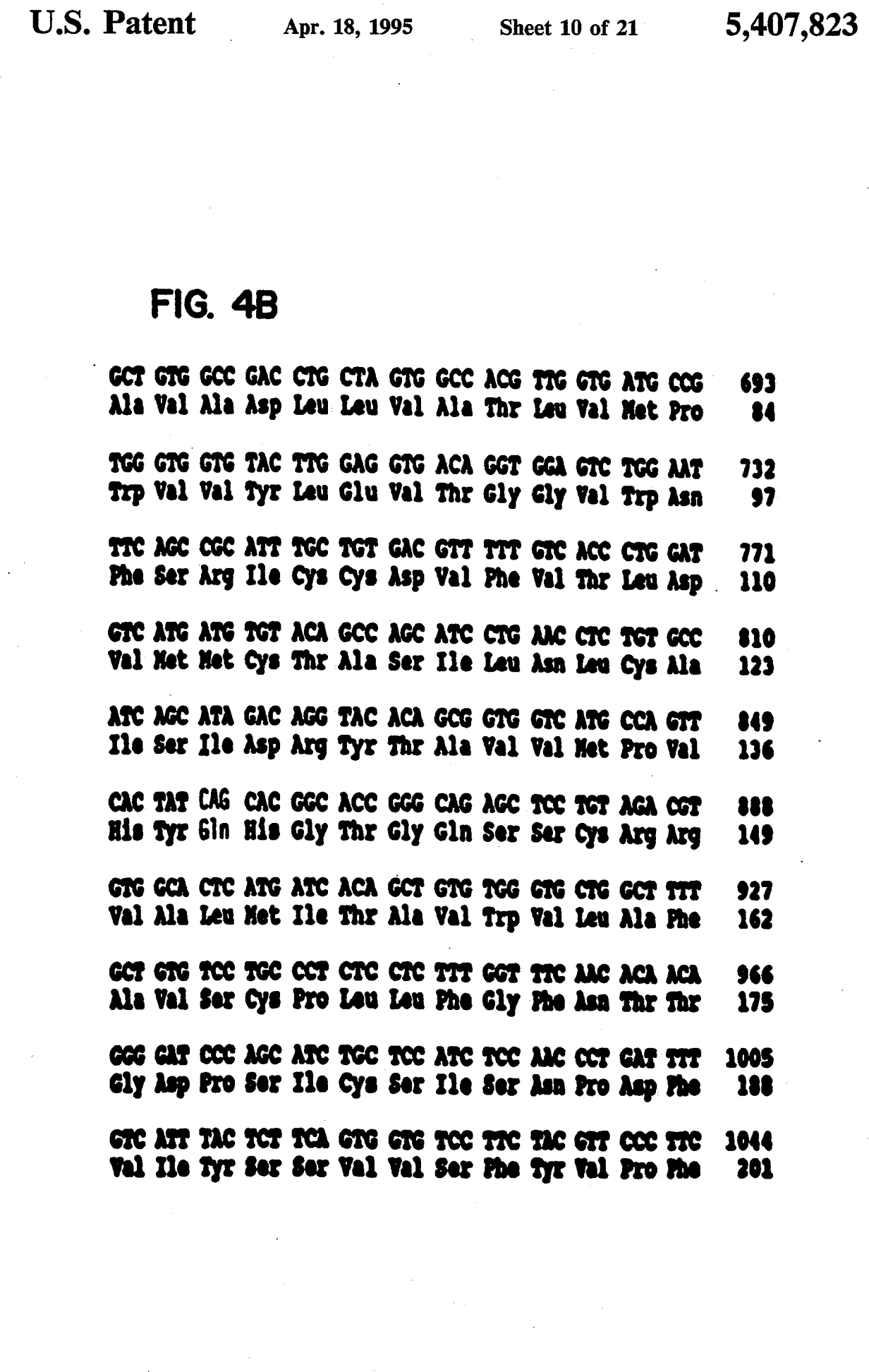

| | | | | | | | | | | | | | |
|---|---|---|---|---|---|---|---|---|---|---|---|---|---|
| GCT | GTG | GCC | GAC | CTG | CTA | GTG | GCC | ACG | TTG | GTG | ATG | CCG | 693 |
| Ala | Val | Ala | Asp | Leu | Leu | Val | Ala | Thr | Leu | Val | Met | Pro | 84 |
| TGG | GTG | GTG | TAC | TTG | GAG | GTG | ACA | GGT | GGA | GTC | TGG | AAT | 732 |
| Trp | Val | Val | Tyr | Leu | Glu | Val | Thr | Gly | Gly | Val | Trp | Asn | 97 |
| TTC | AGC | CGC | ATT | TGC | TGT | GAC | GTT | TTT | GTC | ACC | CTG | GAT | 771 |
| Phe | Ser | Arg | Ile | Cys | Cys | Asp | Val | Phe | Val | Thr | Leu | Asp | 110 |
| GTC | ATG | ATG | TGT | ACA | GCC | AGC | ATC | CTG | AAC | CTC | TGT | GCC | 810 |
| Val | Met | Met | Cys | Thr | Ala | Ser | Ile | Leu | Asn | Leu | Cys | Ala | 123 |
| ATC | AGC | ATA | GAC | AGG | TAC | ACA | GCG | GTG | GTC | ATG | CCA | GTT | 849 |
| Ile | Ser | Ile | Asp | Arg | Tyr | Thr | Ala | Val | Val | Met | Pro | Val | 136 |
| CAC | TAT | CAG | CAC | GGC | ACC | GGG | CAG | AGC | TCC | TGT | AGA | CGT | 888 |
| His | Tyr | Gln | His | Gly | Thr | Gly | Gln | Ser | Ser | Cys | Arg | Arg | 149 |
| GTG | GCA | CTC | ATG | ATC | ACA | GCT | GTG | TGG | GTG | CTG | GCT | TTT | 927 |
| Val | Ala | Leu | Met | Ile | Thr | Ala | Val | Trp | Val | Leu | Ala | Phe | 162 |
| GCT | GTG | TCC | TGC | CCT | CTC | CTC | TTT | GGT | TTC | AAC | ACA | ACA | 966 |
| Ala | Val | Ser | Cys | Pro | Leu | Leu | Phe | Gly | Phe | Asn | Thr | Thr | 175 |
| GGG | GAT | CCC | AGC | ATC | TGC | TCC | ATC | TCC | AAC | CCT | GAT | TTT | 1005 |
| Gly | Asp | Pro | Ser | Ile | Cys | Ser | Ile | Ser | Asn | Pro | Asp | Phe | 188 |
| GTC | ATT | TAC | TCT | TCA | GTG | GTG | TCC | TTC | TAC | GTT | CCC | TTC | 1044 |
| Val | Ile | Tyr | Ser | Ser | Val | Val | Ser | Phe | Tyr | Val | Pro | Phe | 201 |

FIG. 4C

```
GGG GTG ACT GTC CTG GTC TAT GCC AGG ATC TAC ATA GTC  1083
Gly Val Thr Val Leu Val Tyr Ala Arg Ile Tyr Ile Val   214

CTG AGG CAA AGG CAA AGA AAA CGG ATC CTC ACT CGA CAG  1122
Leu Arg Gln Arg Gln Arg Lys Arg Ile Leu Thr Arg Gln   227

AAC AGC CAG TGC ATC AGT ATC AGA CCT GGC TTT CCT CAG  1161
Asn Ser Gln Cys Ile Ser Ile Arg Pro Gly Phe Pro Gln   240

CAG TCT TCC TGT CTG AGG CTG CAT CCC ATT CGG CAG TTT  1200
Gln Ser Ser Cys Leu Arg Leu His Pro Ile Arg Gln Phe   253

TCA ATA AGG GCC AGG TTT CTG TCA GAT GCC ACA GGA CAA  1239
Ser Ile Arg Ala Arg Phe Leu Ser Asp Ala Thr Gly Gln   266

ATG GAG CAC ATA GAA GAC AAA CAA TAT CCC CAG AAA TGC  1278
Met Glu His Ile Glu Asp Lys Gln Tyr Pro Gln Lys Cys   279

CAG GAC CCC CTT TTG TCA CAC CTG CAG CCC CCC TCA CCT  1317
Gln Asp Pro Leu Leu Ser His Leu Gln Pro Pro Ser Pro   292

GGT CAG ACA CAT GGG GGG CTG AAG CGC TAC TAC AGC ATC  1356
Gly Gln Thr His Gly Gly Leu Lys Arg Tyr Tyr Ser Ile   305

TGC CAA GAC ACT GCC TTG AGA CAC CCA AGC TTG GAA GGC  1395
Cys Gln Asp Thr Ala Leu Arg His Pro Ser Leu Glu Gly   318

GGG GCA GGG ATG AGC CCC GTG GAA AGG ACT CGG AAC TCC  1434
Gly Ala Gly Met Ser Pro Val Glu Arg Thr Arg Asn Ser   331
```

FIG. 4D

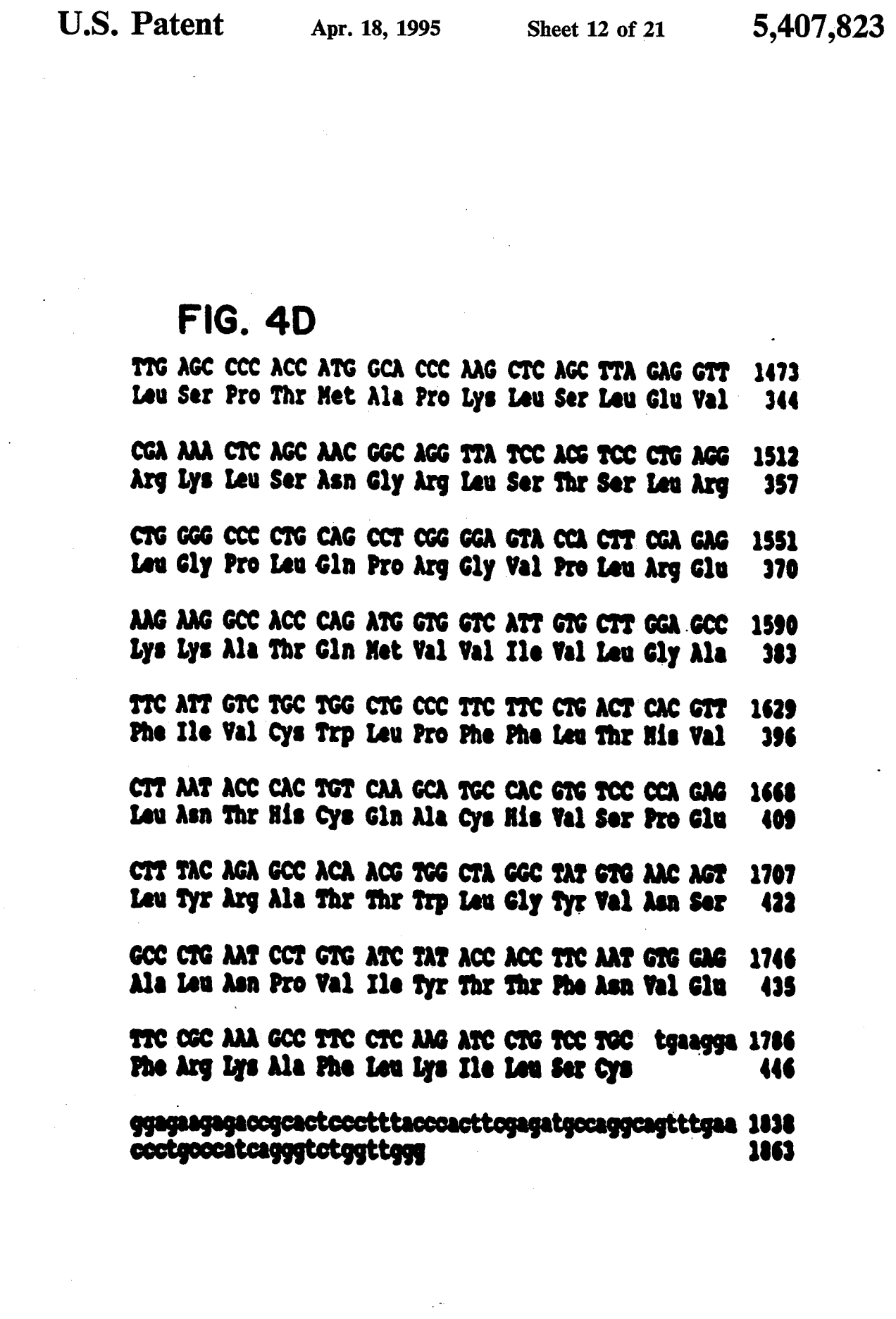

```
TTG AGC CCC ACC ATG GCA CCC AAG CTC AGC TTA GAG GTT  1473
Leu Ser Pro Thr Met Ala Pro Lys Leu Ser Leu Glu Val   344

CGA AAA CTC AGC AAC GGC AGG TTA TCC ACG TCC CTG AGG  1512
Arg Lys Leu Ser Asn Gly Arg Leu Ser Thr Ser Leu Arg   357

CTG GGG CCC CTG CAG CCT CGG GGA GTA CCA CTT CGA GAG  1551
Leu Gly Pro Leu Gln Pro Arg Gly Val Pro Leu Arg Glu   370

AAG AAG GCC ACC CAG ATG GTG GTC ATT GTG CTT GGA GCC  1590
Lys Lys Ala Thr Gln Met Val Val Ile Val Leu Gly Ala   383

TTC ATT GTC TGC TGG CTG CCC TTC TTC CTG ACT CAC GTT  1629
Phe Ile Val Cys Trp Leu Pro Phe Phe Leu Thr His Val   396

CTT AAT ACC CAC TGT CAA GCA TGC CAC GTG TCC CCA GAG  1668
Leu Asn Thr His Cys Gln Ala Cys His Val Ser Pro Glu   409

CTT TAC AGA GCC ACA ACG TGG CTA GGC TAT GTG AAC AGT  1707
Leu Tyr Arg Ala Thr Thr Trp Leu Gly Tyr Val Asn Ser   422

GCC CTG AAT CCT GTG ATC TAT ACC ACC TTC AAT GTG GAG  1746
Ala Leu Asn Pro Val Ile Tyr Thr Thr Phe Asn Val Glu   435

TTC CGC AAA GCC TTC CTC AAG ATC CTG TCC TGC  tgaagga 1786
Phe Arg Lys Ala Phe Leu Lys Ile Leu Ser Cys           446

ggagaagagaccgcactccctttacccacttcgagatgccaggcagtttgaa 1838
ccctgcccatcagggtctggttggg                            1863
```

SPECIFIC BINDING OF $I^{125}$ IODOSULPRIDE (%)

SPECIFIC BINDING OF $I^{125}$ IODOSULPRIDE (%)

A
B
C
D
E
F
OB
Tu
TT
Acb
ICjM
CM
PF
VTA
Hip
MP
Cg
Fr
ICj
MPA
MM
Vl
G
CI
CPu
$^{125}$I- IODOSULPRIDE
D 2 mRNA
D 3 mRNA

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
( A ) LENGTH: 444 amino acids
( B ) TYPE: amino acid
( D ) TOPOLOGY: linear ( i i ) MOLECULE TYPE: protein ( v i i ) IMMEDIATE SOURCE:
( B ) CLONE: D-2 dopaminergic receptor ( x i ) SEQUENCE DESCRIPTION: SEQ ID NO:1:

```
Met Asp Pro Leu Asn Leu Ser Trp Tyr Asp Asp Asp Leu Glu Arg Gln
1               5                   10                  15

Asn Trp Ser Arg Pro Phe Asn Gly Ser Glu Gly Lys Ala Asp Arg Pro
            20                  25                  30

His Tyr Asn Tyr Tyr Ala Met Leu Leu Thr Leu Leu Ile Phe Ile Ile
        35                  40                  45

Val Phe Gly Asn Val Leu Val Cys Met Ala Val Ser Arg Glu Lys Ala
    50                  55                  60

Leu Gln Thr Thr Thr Asn Tyr Leu Ile Val Ser Leu Ala Val Ala Asp
65                  70                  75                  80

Leu Leu Val Ala Thr Leu Val Met Pro Trp Val Val Tyr Leu Glu Val
                85                  90                  95

Val Gly Glu Trp Lys Phe Ser Arg Ile His Cys Asp Ile Phe Val Thr
            100                 105                 110

Leu Asp Val Met Met Cys Thr Ala Ser Ile Leu Asn Leu Cys Ala Ile
        115                 120                 125
```

-continued

| | | | | | | | | | | | | | | | |
|---|---|---|---|---|---|---|---|---|---|---|---|---|---|---|---|
| Ser | Ile | Asp | Arg | Tyr | Thr | Ala | Val | Ala | Met | Pro | Met | Leu | Tyr | Asn | Thr |
| | 130 | | | | | 135 | | | | | 140 | | | | |
| Arg | Tyr | Ser | Ser | Lys | Arg | Arg | Val | Thr | Val | Met | Ile | Ala | Ile | Val | Trp |
| 145 | | | | | 150 | | | | | 155 | | | | | 160 |
| Val | Leu | Ser | Phe | Thr | Ile | Ser | Cys | Pro | Leu | Leu | Phe | Gly | Leu | Asn | Asn |
| | | | | 165 | | | | | 170 | | | | | 175 | |
| Thr | Asp | Gln | Asn | Glu | Cys | Ile | Ile | Ala | Asn | Pro | Ala | Phe | Val | Val | Tyr |
| | | | 180 | | | | | 185 | | | | | 190 | | |
| Ser | Ser | Ile | Val | Ser | Phe | Tyr | Val | Pro | Phe | Ile | Val | Thr | Leu | Leu | Val |
| | | 195 | | | | | 200 | | | | | 205 | | | |
| Tyr | Ile | Lys | Ile | Tyr | Ile | Val | Leu | Arg | Lys | Arg | Arg | Lys | Arg | Val | Asn |
| | 210 | | | | | 215 | | | | | 220 | | | | |
| Thr | Lys | Arg | Ser | Ser | Arg | Ala | Phe | Arg | Ala | Asn | Leu | Lys | Thr | Pro | Leu |
| 225 | | | | | 230 | | | | | 235 | | | | | 240 |
| Lys | Gly | Asn | Cys | Thr | His | Pro | Glu | Asp | Met | Lys | Leu | Cys | Thr | Val | Ile |
| | | | | 245 | | | | | 250 | | | | | 255 | |
| Met | Lys | Ser | Asn | Gly | Ser | Phe | Pro | Val | Asn | Arg | Arg | Arg | Met | Asp | Ala |
| | | | 260 | | | | | 265 | | | | | 270 | | |
| Ala | Arg | Arg | Ala | Gln | Glu | Leu | Glu | Met | Glu | Met | Leu | Ser | Ser | Thr | Ser |
| | | 275 | | | | | 280 | | | | | 285 | | | |
| Pro | Pro | Glu | Arg | Thr | Arg | Tyr | Ser | Pro | Ile | Pro | Pro | Ser | His | His | Gln |
| | 290 | | | | | 295 | | | | | 300 | | | | |
| Leu | Thr | Leu | Pro | Asp | Pro | Ser | His | His | Gly | Leu | His | Ser | Asn | Pro | Asp |
| 305 | | | | | 310 | | | | | 315 | | | | | 320 |
| Ser | Pro | Ala | Lys | Pro | Glu | Lys | Asn | Gly | His | Ala | Lys | Ile | Val | Asn | Pro |
| | | | | 325 | | | | | 330 | | | | | 335 | |
| Arg | Ile | Ala | Lys | Phe | Phe | Glu | Ile | Gln | Thr | Met | Pro | Asn | Gly | Lys | Thr |
| | | | 340 | | | | | 345 | | | | | 350 | | |
| Arg | Thr | Ser | Leu | Lys | Thr | Met | Ser | Arg | Arg | Lys | Leu | Ser | Gln | Gln | Lys |
| | | 355 | | | | | 360 | | | | | 365 | | | |
| Glu | Lys | Lys | Ala | Thr | Gln | Met | Leu | Ala | Ile | Val | Leu | Gly | Val | Phe | Ile |
| | 370 | | | | | 375 | | | | | 380 | | | | |
| Ile | Cys | Trp | Leu | Pro | Phe | Phe | Ile | Thr | His | Ile | Leu | Asn | Ile | His | Cys |
| 385 | | | | | 390 | | | | | 395 | | | | | 400 |
| Asp | Cys | Asn | Ile | Pro | Pro | Val | Leu | Tyr | Ser | Ala | Phe | Thr | Trp | Leu | Gly |
| | | | | 405 | | | | | 410 | | | | | 415 | |
| Tyr | Val | Asn | Ser | Ala | Val | Asn | Pro | Ile | Ile | Tyr | Thr | Thr | Phe | Asn | Ile |
| | | | 420 | | | | | 425 | | | | | 430 | | |
| Glu | Phe | Arg | Lys | Ala | Phe | Met | Lys | Ile | Leu | His | Cys | | | | |
| | | 435 | | | | | 440 | | | | | | | | |

( 2 ) INFORMATION FOR SEQ ID NO:2:

( i ) SEQUENCE CHARACTERISTICS:
( A ) LENGTH: 446 amino acids
( B ) TYPE: amino acid
( D ) TOPOLOGY: linear ( i i ) MOLECULE TYPE: protein ( v i i ) IMMEDIATE SOURCE:
( B ) CLONE: Variant D-3 dopaminergic receptor ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Ala | Pro | Leu | Ser | Gln | Ile | Ser | Thr | His | Leu | Asn | Ser | Thr | Cys | Gly |
| 1 | | | | 5 | | | | | 10 | | | | | 15 | |
| Ala | Glu | Asn | Ser | Thr | Gly | Val | Asn | Arg | Ala | Arg | Pro | His | Ala | Tyr | Tyr |
| | | | 20 | | | | | 25 | | | | | 30 | | |
| Ala | Leu | Ser | Tyr | Cys | Ala | Leu | Ile | Leu | Ala | Ile | Ile | Phe | Gly | Asn | Gly |

-continued 35 40 45

Leu Val Cys Ala Ala Val Leu Arg Glu Arg Ala Leu Gln Thr Thr Thr
50 55 60

Asn Tyr Leu Val Val Ser Leu Ala Val Ala Asp Leu Leu Val Ala Thr
65 70 75 80

Leu Val Met Pro Trp Val Val Tyr Leu Glu Val Thr Gly Gly Val Trp
85 90 95

Asn Phe Ser Arg Ile Cys Cys Asp Val Phe Val Thr Leu Asp Val Met
100 105 110

Met Cys Thr Ala Ser Ile Leu Asn Leu Cys Ala Ile Ser Ile Asp Arg
115 120 125

Tyr Thr Ala Val Val Met Pro Val His Tyr Glu His Gly Thr Gly Gln
130 135 140

Ser Ser Cys Arg Arg Val Ala Leu Met Ile Thr Ala Val Trp Val Leu
145 150 155 160

Ala Phe Ala Val Ser Cys Pro Leu Leu Phe Gly Phe Asn Thr Thr Gly
165 170 175

Asp Pro Ser Ile Cys Ser Ile Ser Asn Pro Asp Phe Val Ile Tyr Ser
180 185 190

Ser Val Val Ser Phe Tyr Val Pro Phe Gly Val Thr Val Leu Val Tyr
195 200 205

Ala Arg Ile Tyr Ile Val Leu Arg Gln Arg Gln Arg Lys Arg Ile Leu
210 215 220

Thr Arg Gln Asn Ser Gln Cys Ile Ser Ile Arg Pro Gly Phe Pro Gln
225 230 235 240

Gln Ser Ser Cys Leu Arg Leu His Pro Ile Arg Gln Phe Ser Ile Arg
245 250 255

Ala Arg Phe Leu Ser Asp Ala Thr Gly Gln Met Glu His Ile Glu Asp
260 265 270

Lys Gln Tyr Pro Gln Lys Cys Gln Asp Pro Leu Leu Ser His Leu Gln
275 280 285

Pro Pro Ser Pro Gly Gln Thr His Gly Gly Leu Lys Arg Tyr Tyr Ser
290 295 300

Ile Cys Gln Asp Thr Ala Leu Arg His Pro Ser Leu Glu Gly Gly Ala
305 310 315 320

Gly Met Ser Pro Val Glu Arg Thr Arg Asn Ser Leu Ser Pro Thr Met
325 330 335

Ala Pro Lys Leu Ser Leu Glu Val Arg Lys Leu Ser Asn Gly Arg Leu
340 345 350

Ser Thr Ser Leu Arg Leu Gly Pro Leu Gln Pro Arg Gly Val Pro Leu
355 360 365

Arg Glu Lys Lys Ala Thr Gln Met Val Val Ile Val Leu Gly Ala Phe
370 375 380

Ile Val Cys Trp Leu Pro Phe Phe Leu Thr His Val Leu Asn Thr His
385 390 395 400

Cys Gln Ala Cys His Val Ser Pro Glu Leu Tyr Arg Ala Thr Thr Trp
405 410 415

Leu Gly Tyr Val Asn Ser Ala Leu Asn Pro Val Ile Tyr Thr Thr Phe
420 425 430

Asn Val Glu Phe Arg Lys Ala Phe Leu Lys Ile Leu Ser Cys
435 440 445

( 2 ) INFORMATION FOR SEQ ID NO:3:

( i ) SEQUENCE CHARACTERISTICS:

( A ) LENGTH: 446 amino acids

-continued ( B ) TYPE: amino acid
( D ) TOPOLOGY: linear ( i i ) MOLECULE TYPE: protein ( v i i ) IMMEDIATE SOURCE:
( B ) CLONE: D-3 dopaminergic receptor ( x i ) SEQUENCE DESCRIPTION: SEQ ID NO:3:

| | | | | | | | | | | | | | | | |
|---|---|---|---|---|---|---|---|---|---|---|---|---|---|---|---|
| Met | Ala | Pro | Leu | Ser | Gln | Ile | Ser | Thr | His | Leu | Asn | Ser | Thr | Cys | Gly |
| 1 | | | | 5 | | | | | 10 | | | | | 15 | |
| Ala | Glu | Asn | Ser | Thr | Gly | Val | Asn | Arg | Ala | Arg | Pro | His | Ala | Tyr | Tyr |
| | | | 20 | | | | | 25 | | | | | 30 | | |
| Ala | Leu | Ser | Tyr | Cys | Ala | Leu | Ile | Leu | Ala | Ile | Ile | Phe | Gly | Asn | Gly |
| | | 35 | | | | | 40 | | | | | 45 | | | |
| Leu | Val | Cys | Ala | Ala | Val | Leu | Arg | Glu | Arg | Ala | Leu | Gln | Thr | Thr | Thr |
| | 50 | | | | | 55 | | | | | 60 | | | | |
| Asn | Tyr | Leu | Val | Val | Ser | Leu | Ala | Val | Ala | Asp | Leu | Leu | Val | Ala | Thr |
| 65 | | | | | 70 | | | | | 75 | | | | | 80 |
| Leu | Val | Met | Pro | Trp | Val | Val | Tyr | Leu | Glu | Val | Thr | Gly | Gly | Val | Trp |
| | | | | 85 | | | | | 90 | | | | | 95 | |
| Asn | Phe | Ser | Arg | Ile | Cys | Cys | Asp | Val | Phe | Val | Thr | Leu | Asp | Val | Met |
| | | | 100 | | | | | 105 | | | | | 110 | | |
| Met | Cys | Thr | Ala | Ser | Ile | Leu | Asn | Leu | Cys | Ala | Ile | Ser | Ile | Asp | Arg |
| | | 115 | | | | | 120 | | | | | 125 | | | |
| Tyr | Thr | Ala | Val | Val | Met | Pro | Val | His | Tyr | Gln | His | Gly | Thr | Gly | Gln |
| | 130 | | | | | 135 | | | | | 140 | | | | |
| Ser | Ser | Cys | Arg | Arg | Val | Ala | Leu | Met | Ile | Thr | Ala | Val | Trp | Val | Leu |
| 145 | | | | | 150 | | | | | 155 | | | | | 160 |
| Ala | Phe | Ala | Val | Ser | Cys | Pro | Leu | Leu | Phe | Gly | Phe | Asn | Thr | Thr | Gly |
| | | | | 165 | | | | | 170 | | | | | 175 | |
| Asp | Pro | Ser | Ile | Cys | Ser | Ile | Ser | Asn | Pro | Asp | Phe | Val | Ile | Tyr | Ser |
| | | | 180 | | | | | 185 | | | | | 190 | | |
| Ser | Val | Val | Ser | Phe | Tyr | Val | Pro | Phe | Gly | Val | Thr | Val | Leu | Val | Tyr |
| | | 195 | | | | | 200 | | | | | 205 | | | |
| Ala | Arg | Ile | Tyr | Ile | Val | Leu | Arg | Gln | Arg | Gln | Arg | Lys | Arg | Ile | Leu |
| | 210 | | | | | 215 | | | | | 220 | | | | |
| Thr | Arg | Gln | Asn | Ser | Gln | Cys | Ile | Ser | Ile | Arg | Pro | Gly | Phe | Pro | Gln |
| 225 | | | | | 230 | | | | | 235 | | | | | 240 |
| Gln | Ser | Ser | Cys | Leu | Arg | Leu | His | Pro | Ile | Arg | Gln | Phe | Ser | Ile | Arg |
| | | | | 245 | | | | | 250 | | | | | 255 | |
| Ala | Arg | Phe | Leu | Ser | Asp | Ala | Thr | Gly | Gln | Met | Glu | His | Ile | Glu | Asp |
| | | | 260 | | | | | 265 | | | | | 270 | | |
| Lys | Gln | Tyr | Pro | Gln | Lys | Cys | Gln | Asp | Pro | Leu | Leu | Ser | His | Leu | Gln |
| | | 275 | | | | | 280 | | | | | 285 | | | |
| Pro | Pro | Ser | Pro | Gly | Gln | Thr | His | Gly | Gly | Leu | Lys | Arg | Tyr | Tyr | Ser |
| | 290 | | | | | 295 | | | | | 300 | | | | |
| Ile | Cys | Gln | Asp | Thr | Ala | Leu | Arg | His | Pro | Ser | Leu | Glu | Gly | Gly | Ala |
| 305 | | | | | 310 | | | | | 315 | | | | | 320 |
| Gly | Met | Ser | Pro | Val | Glu | Arg | Thr | Arg | Asn | Ser | Leu | Ser | Pro | Thr | Met |
| | | | | 325 | | | | | 330 | | | | | 335 | |
| Ala | Pro | Lys | Leu | Ser | Leu | Glu | Val | Arg | Lys | Leu | Ser | Asn | Gly | Arg | Leu |
| | | | 340 | | | | | 345 | | | | | 350 | | |
| Ser | Thr | Ser | Leu | Arg | Leu | Gly | Pro | Leu | Gln | Pro | Arg | Gly | Val | Pro | Leu |
| | | 355 | | | | | 360 | | | | | 365 | | | |
| Arg | Glu | Lys | Lys | Ala | Thr | Gln | Met | Val | Val | Ile | Val | Leu | Gly | Ala | Phe |
| | 370 | | | | | 375 | | | | | 380 | | | | |

-continued

```
Ile Val Cys Trp Leu Pro Phe Phe Leu Thr His Val Leu Asn Thr His
385                 390                 395                 400

Cys Gln Ala Cys His Val Ser Pro Glu Leu Tyr Arg Ala Thr Thr Trp
                405                 410                 415

Leu Gly Tyr Val Asn Ser Ala Leu Asn Pro Val Ile Tyr Thr Thr Phe
            420                 425                 430

Asn Val Glu Phe Arg Lys Ala Phe Leu Lys Ile Leu Ser Cys
        435                 440                 445
```

( 2 ) INFORMATION FOR SEQ ID NO:4:

( i ) SEQUENCE CHARACTERISTICS:
( A ) LENGTH: 1863 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Nucleic acid sequence of variant D-3 dopaminergic receptor ( i x ) FEATURE:
( A ) NAME/KEY: CDS
( B ) LOCATION: 442..1779

( x i ) SEQUENCE DESCRIPTION: SEQ ID NO:4:

```
GCTAGCCTTG CCTTCACTGC TAATATAGCC AGGAAGCCTT CTTGTTATCT AATATAGCCA      60

GGAAGCCTTC TTGTTATCTA ACTGTGCTTA CCCACAATCA TACCATCCTC GACCACTCCC     120

CAACTCCCAT TTCTGATTTA CTTTTCTCCA AAAAGCATAA TATCGCAGAA CAGGTCTTAT     180

CTTGATTATA AATCTTCTCC CCCCCCCCCA ACCCCATAGA GGTTTCATAA GGGAAGAAAT     240

GTCTGTTCCT TTCCTAACTG TATTTCTGGT TCTATAGCAC TGCCTGCTCT ATATAGAAAT     300

GTTCCATCGA TATTTGTAGA CATGAAACAT TTTAAACTGT ATGTATGTAA CATATCCCAG     360

CTCTGAAGAG CCTGATTTAG CCCACATTGC TGTCTGTCTT TTCCTAGGAA CATTTTGGAG     420

TCGCGTTCCT CTGTGTGGGC C ATG GCA CCT CTG AGC CAG ATA AGC ACC CAC      471
                        Met Ala Pro Leu Ser Gln Ile Ser Thr His
                          1               5                  10

CTC AAC TCC ACC TGC GGG GCA GAA AAC TCC ACT GGC GTC AAC CGG GCC      519
Leu Asn Ser Thr Cys Gly Ala Glu Asn Ser Thr Gly Val Asn Arg Ala
                15                  20                  25

CGT CCG CAC GCC TAC TAC GCC CTG TCC TAC TGT GCT CTC ATC CTA GCC      567
Arg Pro His Ala Tyr Tyr Ala Leu Ser Tyr Cys Ala Leu Ile Leu Ala
            30                  35                  40

ATC ATC TTT GGC AAC GGC CTG GTA TGT GCT GCT GTG CTG AGG GAG CGT      615
Ile Ile Phe Gly Asn Gly Leu Val Cys Ala Ala Val Leu Arg Glu Arg
        45                  50                  55

GCC CTG CAG ACC ACC ACC AAC TAC CTA GTG GTG AGC CTG GCT GTG GCC      663
Ala Leu Gln Thr Thr Thr Asn Tyr Leu Val Val Ser Leu Ala Val Ala
    60                  65                  70

GAC CTG CTA GTG GCC ACG TTG GTG ATG CCG TGG GTG GTG TAC TTG GAG      711
Asp Leu Leu Val Ala Thr Leu Val Met Pro Trp Val Val Tyr Leu Glu
 75                  80                  85                  90

GTG ACA GGT GGA GTC TGG AAT TTC AGC CGC ATT TGC TGT GAC GTT TTT      759
Val Thr Gly Gly Val Trp Asn Phe Ser Arg Ile Cys Cys Asp Val Phe
                 95                 100                 105

GTC ACC CTG GAT GTC ATG ATG TGT ACA GCC AGC ATC CTG AAC CTC TGT      807
Val Thr Leu Asp Val Met Met Cys Thr Ala Ser Ile Leu Asn Leu Cys
            110                 115                 120

GCC ATC AGC ATA GAC AGG TAC ACA GCG GTG GTC ATG CCA GTT CAC TAT      855
Ala Ile Ser Ile Asp Arg Tyr Thr Ala Val Val Met Pro Val His Tyr
        125                 130                 135
```

-continued

GAG CAC GGC ACC GGG CAG AGC TCC TGT AGA CGT GTG GCA CTC ATG ATC 903
Glu His Gly Thr Gly Gln Ser Ser Cys Arg Arg Val Ala Leu Met Ile
140 145 150

ACA GCT GTG TGG GTG CTG GCT TTT GCT GTG TCC TGC CCT CTC CTC TTT 951
Thr Ala Val Trp Val Leu Ala Phe Ala Val Ser Cys Pro Leu Leu Phe
155 160 165 170

GGT TTC AAC ACA ACA GGG GAT CCC AGC ATC TGC TCC ATC TCC AAC CCT 999
Gly Phe Asn Thr Thr Gly Asp Pro Ser Ile Cys Ser Ile Ser Asn Pro
175 180 185

GAT TTT GTC ATT TAC TCT TCA GTG GTG TCC TTC TAC GTT CCC TTC GGG 1047
Asp Phe Val Ile Tyr Ser Ser Val Val Ser Phe Tyr Val Pro Phe Gly
190 195 200

GTG ACT GTC CTG GTC TAT GCC AGG ATC TAC ATA GTC CTG AGG CAA AGG 1095
Val Thr Val Leu Val Tyr Ala Arg Ile Tyr Ile Val Leu Arg Gln Arg
205 210 215

CAA AGA AAA CGG ATC CTC ACT CGA CAG AAC AGC CAG TGC ATC AGT ATC 1143
Gln Arg Lys Arg Ile Leu Thr Arg Gln Asn Ser Gln Cys Ile Ser Ile
220 225 230

AGA CCT GGC TTT CCT CAG CAG TCT TCC TGT CTG AGG CTG CAT CCC ATT 1191
Arg Pro Gly Phe Pro Gln Gln Ser Ser Cys Leu Arg Leu His Pro Ile
235 240 245 250

CGG CAG TTT TCA ATA AGG GCC AGG TTT CTG TCA GAT GCC ACA GGA CAA 1239
Arg Gln Phe Ser Ile Arg Ala Arg Phe Leu Ser Asp Ala Thr Gly Gln
255 260 265

ATG GAG CAC ATA GAA GAC AAA CAA TAT CCC CAG AAA TGC CAG GAC CCC 1287
Met Glu His Ile Glu Asp Lys Gln Tyr Pro Gln Lys Cys Gln Asp Pro
270 275 280

CTT TTG TCA CAC CTG CAG CCC CCC TCA CCT GGT CAG ACA CAT GGG GGG 1335
Leu Leu Ser His Leu Gln Pro Pro Ser Pro Gly Gln Thr His Gly Gly
285 290 295

CTG AAG CGC TAC TAC AGC ATC TGC CAA GAC ACT GCC TTG AGA CAC CCA 1383
Leu Lys Arg Tyr Tyr Ser Ile Cys Gln Asp Thr Ala Leu Arg His Pro
300 305 310

AGC TTG GAA GGC GGG GCA GGG ATG AGC CCC GTG GAA AGG ACT CGG AAC 1431
Ser Leu Glu Gly Gly Ala Gly Met Ser Pro Val Glu Arg Thr Arg Asn
315 320 325 330

TCC TTG AGC CCC ACC ATG GCA CCC AAG CTC AGC TTA GAG GTT CGA AAA 1479
Ser Leu Ser Pro Thr Met Ala Pro Lys Leu Ser Leu Glu Val Arg Lys
335 340 345

CTC AGC AAC GGC AGG TTA TCC ACG TCC CTG AGG CTG GGG CCC CTG CAG 1527
Leu Ser Asn Gly Arg Leu Ser Thr Ser Leu Arg Leu Gly Pro Leu Gln
350 355 360

CCT CGG GGA GTA CCA CTT CGA GAG AAG AAG GCC ACC CAG ATG GTG GTC 1575
Pro Arg Gly Val Pro Leu Arg Glu Lys Lys Ala Thr Gln Met Val Val
365 370 375

ATT GTG CTT GGA GCC TTC ATT GTC TGC TGG CTG CCC TTC TTC CTG ACT 1623
Ile Val Leu Gly Ala Phe Ile Val Cys Trp Leu Pro Phe Phe Leu Thr
380 385 390

CAC GTT CTT AAT ACC CAC TGT CAA GCA TGC CAC GTG TCC CCA GAG CTT 1671
His Val Leu Asn Thr His Cys Gln Ala Cys His Val Ser Pro Glu Leu
395 400 405 410

TAC AGA GCC ACA ACG TGG CTA GGC TAT GTG AAC AGT GCC CTG AAT CCT 1719
Tyr Arg Ala Thr Thr Trp Leu Gly Tyr Val Asn Ser Ala Leu Asn Pro
415 420 425

GTG ATC TAT ACC ACC TTC AAT GTG GAG TTC CGC AAA GCC TTC CTC AAG 1767
Val Ile Tyr Thr Thr Phe Asn Val Glu Phe Arg Lys Ala Phe Leu Lys
430 435 440

ATC CTG TCC TGC TGAAGGAGGA GAAGAGACCG CACTCCCTTT ACCCACTTCG 1819
Ile Leu Ser Cys
445

AGATGCCAGG CAGTTTGAAC CCTGCCCATC AGGGTCTGGT TGGG 1863

-continued ( 2 ) INFORMATION FOR SEQ ID NO:5:

( i ) SEQUENCE CHARACTERISTICS:
( A ) LENGTH: 1863 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Nucleic acid sequence for D-3 dopaminergic receptor ( i x ) FEATURE:
( A ) NAME/KEY: CDS
( B ) LOCATION: 442..1779

( x i ) SEQUENCE DESCRIPTION: SEQ ID NO:5:

GCTAGCCTTG CCTTCACTGC TAATATAGCC AGGAAGCCTT CTTGTTATCT AATATAGCCA 60

GGAAGCCTTC TTGTTATCTA ACTGTGCTTA CCCACAATCA TACCATCCTC GACCACTCCC 120

CAACTCCCAT TTCTGATTTA CTTTTCTCCA AAAAGCATAA TATCGCAGAA CAGGTCTTAT 180

CTTGATTATA AATCTTCTCC CCCCCCCCCA ACCCCATAGA GGTTTCATAA GGGAAGAAAT 240

GTCTGTTCCT TTCCTAACTG TATTTCTGGT TCTATAGCAC TGCCTGCTCT ATATAGAAAT 300

GTTCCATCGA TATTTGTAGA CATGAAACAT TTTAAACTGT ATGTATGTAA CATATCCCAG 360

CTCTGAAGAG CCTGATTTAG CCCACATTGC TGTCTGTCTT TTCCTAGGAA CATTTTGGAG 420

TCGCGTTCCT CTGTGTGGGC C ATG GCA CCT CTG AGC CAG ATA AGC ACC CAC 471
Met Ala Pro Leu Ser Gln Ile Ser Thr His
1 5 10

CTC AAC TCC ACC TGC GGG GCA GAA AAC TCC ACT GGC GTC AAC CGG GCC 519
Leu Asn Ser Thr Cys Gly Ala Glu Asn Ser Thr Gly Val Asn Arg Ala
15 20 25

CGT CCG CAC GCC TAC TAC GCC CTG TCC TAC TGT GCT CTC ATC CTA GCC 567
Arg Pro His Ala Tyr Tyr Ala Leu Ser Tyr Cys Ala Leu Ile Leu Ala
30 35 40

ATC ATC TTT GGC AAC GGC CTG GTA TGT GCT GCT GTG CTG AGG GAG CGT 615
Ile Ile Phe Gly Asn Gly Leu Val Cys Ala Ala Val Leu Arg Glu Arg
45 50 55

GCC CTG CAG ACC ACC ACC AAC TAC CTA GTG GTG AGC CTG GCT GTG GCC 663
Ala Leu Gln Thr Thr Thr Asn Tyr Leu Val Val Ser Leu Ala Val Ala
60 65 70

GAC CTG CTA GTG GCC ACG TTG GTG ATG CCG TGG GTG GTG TAC TTG GAG 711
Asp Leu Leu Val Ala Thr Leu Val Met Pro Trp Val Val Tyr Leu Glu
75 80 85 90

GTG ACA GGT GGA GTC TGG AAT TTC AGC CGC ATT TGC TGT GAC GTT TTT 759
Val Thr Gly Gly Val Trp Asn Phe Ser Arg Ile Cys Cys Asp Val Phe
95 100 105

GTC ACC CTG GAT GTC ATG ATG TGT ACA GCC AGC ATC CTG AAC CTC TGT 807
Val Thr Leu Asp Val Met Met Cys Thr Ala Ser Ile Leu Asn Leu Cys
110 115 120

GCC ATC AGC ATA GAC AGG TAC ACA GCG GTG GTC ATG CCA GTT CAC TAT 855
Ala Ile Ser Ile Asp Arg Tyr Thr Ala Val Val Met Pro Val His Tyr
125 130 135

CAG CAC GGC ACC GGG CAG AGC TCC TGT AGA CGT GTG GCA CTC ATG ATC 903
Gln His Gly Thr Gly Gln Ser Ser Cys Arg Arg Val Ala Leu Met Ile
140 145 150

ACA GCT GTG TGG GTG CTG GCT TTT GCT GTG TCC TGC CCT CTC CTC TTT 951
Thr Ala Val Trp Val Leu Ala Phe Ala Val Ser Cys Pro Leu Leu Phe
155 160 165 170

GGT TTC AAC ACA ACA GGG GAT CCC AGC ATC TGC TCC ATC TCC AAC CCT 999
Gly Phe Asn Thr Thr Gly Asp Pro Ser Ile Cys Ser Ile Ser Asn Pro

-continued

```
                175                     180                     185

GAT TTT GTC ATT TAC TCT TCA GTG GTG TCC TTC TAC GTT CCC TTC GGG     1047
Asp Phe Val Ile Tyr Ser Ser Val Val Ser Phe Tyr Val Pro Phe Gly
            190                 195                 200

GTG ACT GTC CTG GTC TAT GCC AGG ATC TAC ATA GTC CTG AGG CAA AGG     1095
Val Thr Val Leu Val Tyr Ala Arg Ile Tyr Ile Val Leu Arg Gln Arg
        205                 210                 215

CAA AGA AAA CGG ATC CTC ACT CGA CAG AAC AGC CAG TGC ATC AGT ATC     1143
Gln Arg Lys Arg Ile Leu Thr Arg Gln Asn Ser Gln Cys Ile Ser Ile
    220                 225                 230

AGA CCT GGC TTT CCT CAG CAG TCT TCC TGT CTG AGG CTG CAT CCC ATT     1191
Arg Pro Gly Phe Pro Gln Gln Ser Ser Cys Leu Arg Leu His Pro Ile
235                 240                 245                 250

CGG CAG TTT TCA ATA AGG GCC AGG TTT CTG TCA GAT GCC ACA GGA CAA     1239
Arg Gln Phe Ser Ile Arg Ala Arg Phe Leu Ser Asp Ala Thr Gly Gln
                255                 260                 265

ATG GAG CAC ATA GAA GAC AAA CAA TAT CCC CAG AAA TGC CAG GAC CCC     1287
Met Glu His Ile Glu Asp Lys Gln Tyr Pro Gln Lys Cys Gln Asp Pro
            270                 275                 280

CTT TTG TCA CAC CTG CAG CCC CCC TCA CCT GGT CAG ACA CAT GGG GGG     1335
Leu Leu Ser His Leu Gln Pro Pro Ser Pro Gly Gln Thr His Gly Gly
        285                 290                 295

CTG AAG CGC TAC TAC AGC ATC TGC CAA GAC ACT GCC TTG AGA CAC CCA     1383
Leu Lys Arg Tyr Tyr Ser Ile Cys Gln Asp Thr Ala Leu Arg His Pro
    300                 305                 310

AGC TTG GAA GGC GGG GCA GGG ATG AGC CCC GTG GAA AGG ACT CGG AAC     1431
Ser Leu Glu Gly Gly Ala Gly Met Ser Pro Val Glu Arg Thr Arg Asn
315                 320                 325                 330

TCC TTG AGC CCC ACC ATG GCA CCC AAG CTC AGC TTA GAG GTT CGA AAA     1479
Ser Leu Ser Pro Thr Met Ala Pro Lys Leu Ser Leu Glu Val Arg Lys
                335                 340                 345

CTC AGC AAC GGC AGG TTA TCC ACG TCC CTG AGG CTG GGG CCC CTG CAG     1527
Leu Ser Asn Gly Arg Leu Ser Thr Ser Leu Arg Leu Gly Pro Leu Gln
            350                 355                 360

CCT CGG GGA GTA CCA CTT CGA GAG AAG AAG GCC ACC CAG ATG GTG GTC     1575
Pro Arg Gly Val Pro Leu Arg Glu Lys Lys Ala Thr Gln Met Val Val
        365                 370                 375

ATT GTG CTT GGA GCC TTC ATT GTC TGC TGG CTG CCC TTC TTC CTG ACT     1623
Ile Val Leu Gly Ala Phe Ile Val Cys Trp Leu Pro Phe Phe Leu Thr
    380                 385                 390

CAC GTT CTT AAT ACC CAC TGT CAA GCA TGC CAC GTG TCC CCA GAG CTT     1671
His Val Leu Asn Thr His Cys Gln Ala Cys His Val Ser Pro Glu Leu
395                 400                 405                 410

TAC AGA GCC ACA ACG TGG CTA GGC TAT GTG AAC AGT GCC CTG AAT CCT     1719
Tyr Arg Ala Thr Thr Trp Leu Gly Tyr Val Asn Ser Ala Leu Asn Pro
                415                 420                 425

GTG ATC TAT ACC ACC TTC AAT GTG GAG TTC CGC AAA GCC TTC CTC AAG     1767
Val Ile Tyr Thr Thr Phe Asn Val Glu Phe Arg Lys Ala Phe Leu Lys
            430                 435                 440

ATC CTG TCC TGC TGAAGGAGGA GAAGAGACCG CACTCCCTTT ACCCACTTCG         1819
Ile Leu Ser Cys
        445

AGATGCCAGG CAGTTTGAAC CCTGCCCATC AGGGTCTGGT TGGG                    1863
```

( 2 ) INFORMATION FOR SEQ ID NO:6:

( i ) SEQUENCE CHARACTERISTICS:

( A ) LENGTH: 1338 base pairs ( B ) TYPE: nucleic acid ( C ) STRANDEDNESS: single ( D ) TOPOLOGY: linear ( i i ) MOLECULE TYPE: DNA (genomic)

-continued ( v i i ) IMMEDIATE SOURCE:
( B ) CLONE: Coding sequence for variant D-3 dopaminergic receptor ( i x ) FEATURE:
( A ) NAME/KEY: CDS
( B ) LOCATION: 1..1338

( x i ) SEQUENCE DESCRIPTION: SEQ ID NO:6:

ATG GCA CCT CTG AGC CAG ATA AGC ACC CAC CTC AAC TCC ACC TGC GGG 48
Met Ala Pro Leu Ser Gln Ile Ser Thr His Leu Asn Ser Thr Cys Gly
1 5 10 15

GCA GAA AAC TCC ACT GGC GTC AAC CGG GCC CGT CCG CAC GCC TAC TAC 96
Ala Glu Asn Ser Thr Gly Val Asn Arg Ala Arg Pro His Ala Tyr Tyr
20 25 30

GCC CTG TCC TAC TGT GCT CTC ATC CTA GCC ATC ATC TTT GGC AAC GGC 144
Ala Leu Ser Tyr Cys Ala Leu Ile Leu Ala Ile Ile Phe Gly Asn Gly
35 40 45

CTG GTA TGT GCT GCT GTG CTG AGG GAG CGT GCC CTG CAG ACC ACC ACC 192
Leu Val Cys Ala Ala Val Leu Arg Glu Arg Ala Leu Gln Thr Thr Thr
50 55 60

AAC TAC CTA GTG GTG AGC CTG GCT GTG GCC GAC CTG CTA GTG GCC ACG 240
Asn Tyr Leu Val Val Ser Leu Ala Val Ala Asp Leu Leu Val Ala Thr
65 70 75 80

TTG GTG ATG CCG TGG GTG GTG TAC TTG GAG GTG ACA GGT GGA GTC TGG 288
Leu Val Met Pro Trp Val Val Tyr Leu Glu Val Thr Gly Gly Val Trp
85 90 95

AAT TTC AGC CGC ATT TGC TGT GAC GTT TTT GTC ACC CTG GAT GTC ATG 336
Asn Phe Ser Arg Ile Cys Cys Asp Val Phe Val Thr Leu Asp Val Met
100 105 110

ATG TGT ACA GCC AGC ATC CTG AAC CTC TGT GCC ATC AGC ATA GAC AGG 384
Met Cys Thr Ala Ser Ile Leu Asn Leu Cys Ala Ile Ser Ile Asp Arg
115 120 125

TAC ACA GCG GTG GTC ATG CCA GTT CAC TAT GAG CAC GGC ACC GGG CAG 432
Tyr Thr Ala Val Val Met Pro Val His Tyr Glu His Gly Thr Gly Gln
130 135 140

AGC TCC TGT AGA CGT GTG GCA CTC ATG ATC ACA GCT GTG TGG GTG CTG 480
Ser Ser Cys Arg Arg Val Ala Leu Met Ile Thr Ala Val Trp Val Leu
145 150 155 160

GCT TTT GCT GTG TCC TGC CCT CTC CTC TTT GGT TTC AAC ACA ACA GGG 528
Ala Phe Ala Val Ser Cys Pro Leu Leu Phe Gly Phe Asn Thr Thr Gly
165 170 175

GAT CCC AGC ATC TGC TCC ATC TCC AAC CCT GAT TTT GTC ATT TAC TCT 576
Asp Pro Ser Ile Cys Ser Ile Ser Asn Pro Asp Phe Val Ile Tyr Ser
180 185 190

TCA GTG GTG TCC TTC TAC GTT CCC TTC GGG GTG ACT GTC CTG GTC TAT 624
Ser Val Val Ser Phe Tyr Val Pro Phe Gly Val Thr Val Leu Val Tyr
195 200 205

GCC AGG ATC TAC ATA GTC CTG AGG CAA AGG CAA AGA AAA CGG ATC CTC 672
Ala Arg Ile Tyr Ile Val Leu Arg Gln Arg Gln Arg Lys Arg Ile Leu
210 215 220

ACT CGA CAG AAC AGC CAG TGC ATC AGT ATC AGA CCT GGC TTT CCT CAG 720
Thr Arg Gln Asn Ser Gln Cys Ile Ser Ile Arg Pro Gly Phe Pro Gln
225 230 235 240

CAG TCT TCC TGT CTG AGG CTG CAT CCC ATT CGG CAG TTT TCA ATA AGG 768
Gln Ser Ser Cys Leu Arg Leu His Pro Ile Arg Gln Phe Ser Ile Arg
245 250 255

GCC AGG TTT CTG TCA GAT GCC ACA GGA CAA ATG GAG CAC ATA GAA GAC 816
Ala Arg Phe Leu Ser Asp Ala Thr Gly Gln Met Glu His Ile Glu Asp
260 265 270

AAA CAA TAT CCC CAG AAA TGC CAG GAC CCC CTT TTG TCA CAC CTG CAG 864
Lys Gln Tyr Pro Gln Lys Cys Gln Asp Pro Leu Leu Ser His Leu Gln
275 280 285

-continued

CCC CCC TCA CCT GGT CAG ACA CAT GGG GGG CTG AAG CGC TAC TAC AGC 912
Pro Pro Ser Pro Gly Gln Thr His Gly Gly Leu Lys Arg Tyr Tyr Ser
290 295 300

ATC TGC CAA GAC ACT GCC TTG AGA CAC CCA AGC TTG GAA GGC GGG GCA 960
Ile Cys Gln Asp Thr Ala Leu Arg His Pro Ser Leu Glu Gly Gly Ala
305 310 315 320

GGG ATG AGC CCC GTG GAA AGG ACT CGG AAC TCC TTG AGC CCC ACC ATG 1008
Gly Met Ser Pro Val Glu Arg Thr Arg Asn Ser Leu Ser Pro Thr Met
325 330 335

GCA CCC AAG CTC AGC TTA GAG GTT CGA AAA CTC AGC AAC GGC AGG TTA 1056
Ala Pro Lys Leu Ser Leu Glu Val Arg Lys Leu Ser Asn Gly Arg Leu
340 345 350

TCC ACG TCC CTG AGG CTG GGG CCC CTG CAG CCT CGG GGA GTA CCA CTT 1104
Ser Thr Ser Leu Arg Leu Gly Pro Leu Gln Pro Arg Gly Val Pro Leu
355 360 365

CGA GAG AAG AAG GCC ACC CAG ATG GTG GTC ATT GTG CTT GGA GCC TTC 1152
Arg Glu Lys Lys Ala Thr Gln Met Val Val Ile Val Leu Gly Ala Phe
370 375 380

ATT GTC TGC TGG CTG CCC TTC TTC CTG ACT CAC GTT CTT AAT ACC CAC 1200
Ile Val Cys Trp Leu Pro Phe Phe Leu Thr His Val Leu Asn Thr His
385 390 395 400

TGT CAA GCA TGC CAC GTG TCC CCA GAG CTT TAC AGA GCC ACA ACG TGG 1248
Cys Gln Ala Cys His Val Ser Pro Glu Leu Tyr Arg Ala Thr Thr Trp
405 410 415

CTA GGC TAT GTG AAC AGT GCC CTG AAT CCT GTG ATC TAT ACC ACC TTC 1296
Leu Gly Tyr Val Asn Ser Ala Leu Asn Pro Val Ile Tyr Thr Thr Phe
420 425 430

AAT GTG GAG TTC CGC AAA GCC TTC CTC AAG ATC CTG TCC TGC 1338
Asn Val Glu Phe Arg Lys Ala Phe Leu Lys Ile Leu Ser Cys
435 440 445

( 2 ) INFORMATION FOR SEQ ID NO:7:

( i ) SEQUENCE CHARACTERISTICS:
( A ) LENGTH: 1338 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Coding sequence for D-3 dopaminergic receptor ( i x ) FEATURE:
( A ) NAME/KEY: CDS
( B ) LOCATION: 1..1338

( x i ) SEQUENCE DESCRIPTION: SEQ ID NO:7:

ATG GCA CCT CTG AGC CAG ATA AGC ACC CAC CTC AAC TCC ACC TGC GGG 48
Met Ala Pro Leu Ser Gln Ile Ser Thr His Leu Asn Ser Thr Cys Gly
1 5 10 15

GCA GAA AAC TCC ACT GGC GTC AAC CGG GCC CGT CCG CAC GCC TAC TAC 96
Ala Glu Asn Ser Thr Gly Val Asn Arg Ala Arg Pro His Ala Tyr Tyr
20 25 30

GCC CTG TCC TAC TGT GCT CTC ATC CTA GCC ATC ATC TTT GGC AAC GGC 144
Ala Leu Ser Tyr Cys Ala Leu Ile Leu Ala Ile Ile Phe Gly Asn Gly
35 40 45

CTG GTA TGT GCT GCT GTG CTG AGG GAG CGT GCC CTG CAG ACC ACC ACC 192
Leu Val Cys Ala Ala Val Leu Arg Glu Arg Ala Leu Gln Thr Thr Thr
50 55 60

AAC TAC CTA GTG GTG AGC CTG GCT GTG GCC GAC CTG CTA GTG GCC ACG 240
Asn Tyr Leu Val Val Ser Leu Ala Val Ala Asp Leu Leu Val Ala Thr
65 70 75 80

TTG GTG ATG CCG TGG GTG GTG TAC TTG GAG GTG ACA GGT GGA GTC TGG 288

-continued

```
Leu Val Met Pro Trp Val Val Tyr Leu Glu Val Thr Gly Gly Val Trp
                85                  90                  95

AAT TTC AGC CGC ATT TGC TGT GAC GTT TTT GTC ACC CTG GAT GTC ATG        336
Asn Phe Ser Arg Ile Cys Cys Asp Val Phe Val Thr Leu Asp Val Met
            100                 105                 110

ATG TGT ACA GCC AGC ATC CTG AAC CTC TGT GCC ATC AGC ATA GAC AGG        384
Met Cys Thr Ala Ser Ile Leu Asn Leu Cys Ala Ile Ser Ile Asp Arg
        115                 120                 125

TAC ACA GCG GTG GTC ATG CCA GTT CAC TAT CAG CAC GGC ACC GGG CAG        432
Tyr Thr Ala Val Val Met Pro Val His Tyr Gln His Gly Thr Gly Gln
    130                 135                 140

AGC TCC TGT AGA CGT GTG GCA CTC ATG ATC ACA GCT GTG TGG GTG CTG        480
Ser Ser Cys Arg Arg Val Ala Leu Met Ile Thr Ala Val Trp Val Leu
145                 150                 155                 160

GCT TTT GCT GTG TCC TGC CCT CTC CTC TTT GGT TTC AAC ACA ACA GGG        528
Ala Phe Ala Val Ser Cys Pro Leu Leu Phe Gly Phe Asn Thr Thr Gly
                165                 170                 175

GAT CCC AGC ATC TGC TCC ATC TCC AAC CCT GAT TTT GTC ATT TAC TCT        576
Asp Pro Ser Ile Cys Ser Ile Ser Asn Pro Asp Phe Val Ile Tyr Ser
            180                 185                 190

TCA GTG GTG TCC TTC TAC GTT CCC TTC GGG GTG ACT GTC CTG GTC TAT        624
Ser Val Val Ser Phe Tyr Val Pro Phe Gly Val Thr Val Leu Val Tyr
        195                 200                 205

GCC AGG ATC TAC ATA GTC CTG AGG CAA AGG CAA AGA AAA CGG ATC CTC        672
Ala Arg Ile Tyr Ile Val Leu Arg Gln Arg Gln Arg Lys Arg Ile Leu
    210                 215                 220

ACT CGA CAG AAC AGC CAG TGC ATC AGT ATC AGA CCT GGC TTT CCT CAG        720
Thr Arg Gln Asn Ser Gln Cys Ile Ser Ile Arg Pro Gly Phe Pro Gln
225                 230                 235                 240

CAG TCT TCC TGT CTG AGG CTG CAT CCC ATT CGG CAG TTT TCA ATA AGG        768
Gln Ser Ser Cys Leu Arg Leu His Pro Ile Arg Gln Phe Ser Ile Arg
                245                 250                 255

GCC AGG TTT CTG TCA GAT GCC ACA GGA CAA ATG GAG CAC ATA GAA GAC        816
Ala Arg Phe Leu Ser Asp Ala Thr Gly Gln Met Glu His Ile Glu Asp
            260                 265                 270

AAA CAA TAT CCC CAG AAA TGC CAG GAC CCC CTT TTG TCA CAC CTG CAG        864
Lys Gln Tyr Pro Gln Lys Cys Gln Asp Pro Leu Leu Ser His Leu Gln
        275                 280                 285

CCC CCC TCA CCT GGT CAG ACA CAT GGG GGG CTG AAG CGC TAC TAC AGC        912
Pro Pro Ser Pro Gly Gln Thr His Gly Gly Leu Lys Arg Tyr Tyr Ser
    290                 295                 300

ATC TGC CAA GAC ACT GCC TTG AGA CAC CCA AGC TTG GAA GGC GGG GCA        960
Ile Cys Gln Asp Thr Ala Leu Arg His Pro Ser Leu Glu Gly Gly Ala
305                 310                 315                 320

GGG ATG AGC CCC GTG GAA AGG ACT CGG AAC TCC TTG AGC CCC ACC ATG       1008
Gly Met Ser Pro Val Glu Arg Thr Arg Asn Ser Leu Ser Pro Thr Met
                325                 330                 335

GCA CCC AAG CTC AGC TTA GAG GTT CGA AAA CTC AGC AAC GGC AGG TTA       1056
Ala Pro Lys Leu Ser Leu Glu Val Arg Lys Leu Ser Asn Gly Arg Leu
            340                 345                 350

TCC ACG TCC CTG AGG CTG GGG CCC CTG CAG CCT CGG GGA GTA CCA CTT       1104
Ser Thr Ser Leu Arg Leu Gly Pro Leu Gln Pro Arg Gly Val Pro Leu
        355                 360                 365

CGA GAG AAG AAG GCC ACC CAG ATG GTG GTC ATT GTG CTT GGA GCC TTC       1152
Arg Glu Lys Lys Ala Thr Gln Met Val Val Ile Val Leu Gly Ala Phe
    370                 375                 380

ATT GTC TGC TGG CTG CCC TTC TTC CTG ACT CAC GTT CTT AAT ACC CAC       1200
Ile Val Cys Trp Leu Pro Phe Phe Leu Thr His Val Leu Asn Thr His
385                 390                 395                 400

TGT CAA GCA TGC CAC GTG TCC CCA GAG CTT TAC AGA GCC ACA ACG TGG       1248
Cys Gln Ala Cys His Val Ser Pro Glu Leu Tyr Arg Ala Thr Thr Trp
                405                 410                 415
```

-continued

```
CTA GGC TAT GTG AAC AGT GCC CTG AAT CCT GTG ATC TAT ACC ACC TTC      1296
Leu Gly Tyr Val Asn Ser Ala Leu Asn Pro Val Ile Tyr Thr Thr Phe
            420                 425                 430

AAT GTG GAG TTC CGC AAA GCC TTC CTC AAG ATC CTG TCC TGC              1338
Asn Val Glu Phe Arg Lys Ala Phe Leu Lys Ile Leu Ser Cys
            435                 440                 445
```

( 2 ) INFORMATION FOR SEQ ID NO:8:

( i ) SEQUENCE CHARACTERISTICS:
( A ) LENGTH: 441 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Oligonucleotide hybridization probe for variant D- 3

( x i ) SEQUENCE DESCRIPTION: SEQ ID NO:8:

```
GCTAGCCTTG CCTTCACTGC TAATATAGCC AGGAAGCCTT CTTGTTATCT AATATAGCCA    60
GGAAGCCTTC TTGTTATCTA ACTGTGCTTA CCCACAATCA TACCATCCTC GACCACTCCC   120
CAACTCCCAT TTCTGATTTA CTTTTCTCCA AAAAGCATAA TATCGCAGAA CAGGTCTTAT   180
CTTGATTATA AATCTTCTCC CCCCCCCCCA ACCCCATAGA GGTTTCATAA GGGAAGAAAT   240
GTCTGTTCCT TTCCTAACTG TATTTCTGGT TCTATAGCAC TGCCTGCTCT ATATAGAAAT   300
GTTCCATCGA TATTTGTAGA CATGAAACAT TTTAAACTGT ATGTATGTAA CATATCCCAG   360
CTCTGAAGAG CCTGATTTAG CCCACATTGC TGTCTGTCTT TTCCTAGGAA CATTTTGGAG   420
TCGCGTTCCT CTGTGTGGGC C                                             441
```

( 2 ) INFORMATION FOR SEQ ID NO:9:

( i ) SEQUENCE CHARACTERISTICS:
( A ) LENGTH: 96 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Oligonucleotide probe for variant D-3 (nucleotides 442-537)

( i x ) FEATURE:
( A ) NAME/KEY: CDS
( B ) LOCATION: 1..96

( x i ) SEQUENCE DESCRIPTION: SEQ ID NO:9:

```
ATG GCA CCT CTG AGC CAG ATA AGC ACC CAC CTC AAC TCC ACC TGC GGG       48
Met Ala Pro Leu Ser Gln Ile Ser Thr His Leu Asn Ser Thr Cys Gly
  1               5                  10                  15

GCA GAA AAC TCC ACT GGC GTC AAC CGG GCC CGT CCG CAC GCC TAC TAC       96
Ala Glu Asn Ser Thr Gly Val Asn Arg Ala Arg Pro His Ala Tyr Tyr
            20                  25                  30
```

( 2 ) INFORMATION FOR SEQ ID NO:10:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

-continued ( v i i ) IMMEDIATE SOURCE:
( B ) CLONE: Oligonucleotide probe for variant D-3
( n u c l e o t i d e s 7 1 8 - 7 5 3 )

( i x ) FEATURE:
( A ) NAME/KEY: CDS
( B ) LOCATION: 1..36

( x i ) SEQUENCE DESCRIPTION: SEQ ID NO:10:

```
GGT GGA GTC TGG AAT TTC AGC CGC ATT TGC TGT GAC        36
Gly Gly Val Trp Asn Phe Ser Arg Ile Cys Cys Asp
  1             5                   10
```

( 2 ) INFORMATION FOR SEQ ID NO:11:

( i ) SEQUENCE CHARACTERISTICS:
( A ) LENGTH: 69 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Oligonucleotide probe for variant D-3
( n u c l e o t i d e s 8 2 0 - 8 8 8 )

( i x ) FEATURE:
( A ) NAME/KEY: CDS
( B ) LOCATION: 1..69

( x i ) SEQUENCE DESCRIPTION: SEQ ID NO:11:

```
GAC AGG TAC ACA GCG GTG GTC ATG CCA GTT CAC TAT GAG CAC GGC ACC        48
Asp Arg Tyr Thr Ala Val Val Met Pro Val His Tyr Glu His Gly Thr
  1             5                   10                  15

GGG CAG AGC TCC TGT AGA CGT                                            69
Gly Gln Ser Ser Cys Arg Arg
             20
```

( 2 ) INFORMATION FOR SEQ ID NO:12:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Oligonucleotide probe for variant D-3
( n u c l e o t i d e s 9 5 8 - 9 9 6 )

( i x ) FEATURE:
( A ) NAME/KEY: CDS
( B ) LOCATION: 1..39

( x i ) SEQUENCE DESCRIPTION: SEQ ID NO:12:

```
AAC ACA ACA GGG GAT CCC AGC ATC TGC TCC ATC TCC AAC        39
Asn Thr Thr Gly Asp Pro Ser Ile Cys Ser Ile Ser Asn
  1             5                   10
```

( 2 ) INFORMATION FOR SEQ ID NO:13:

( i ) SEQUENCE CHARACTERISTICS:
( A ) LENGTH: 171 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Variant D-3 oligonucleotide probe
( n u c l e o t i d e s 1068- 1 2 4 0 )

-continued ( i x ) FEATURE:
( A ) NAME/KEY: CDS
( B ) LOCATION: 1..171

( x i ) SEQUENCE DESCRIPTION: SEQ ID NO:13:

```
AGG ATC TAC ATA GTC CTG AGG CAA AGG CAA AGA AAA CGG ATC CTC ACT     48
Arg Ile Tyr Ile Val Leu Arg Gln Arg Gln Arg Lys Arg Ile Leu Thr
 1               5                  10                  15

CGA CAG AAC AGC CAG TGC ATC AGT ATC AGA CCT GGC TTT CCT CAG CAG     96
Arg Gln Asn Ser Gln Cys Ile Ser Ile Arg Pro Gly Phe Pro Gln Gln
            20                  25                  30

TCT TCC TGT CTG AGG CTG CAT CCC ATT CGG CAG TTT TCA ATA AGG GCC    144
Ser Ser Cys Leu Arg Leu His Pro Ile Arg Gln Phe Ser Ile Arg Ala
        35                  40                  45

AGG TTT CTG TCA GAT GCC ACA GGA CAA                                171
Arg Phe Leu Ser Asp Ala Thr Gly Gln
    50                  55
```

( 2 ) INFORMATION FOR SEQ ID NO:14:

( i ) SEQUENCE CHARACTERISTICS:
( A ) LENGTH: 498 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Variant D-3 oligonucleotide probe
(nucleotides 1068-1566)

( i x ) FEATURE:
( A ) NAME/KEY: CDS
( B ) LOCATION: 1..498

( x i ) SEQUENCE DESCRIPTION: SEQ ID NO:14:

```
AGG ATC TAC ATA GTC CTG AGG CAA AGG CAA AGA AAA CGG ATC CTC ACT     48
Arg Ile Tyr Ile Val Leu Arg Gln Arg Gln Arg Lys Arg Ile Leu Thr
 1               5                  10                  15

CGA CAG AAC AGC CAG TGC ATC AGT ATC AGA CCT GGC TTT CCT CAG CAG     96
Arg Gln Asn Ser Gln Cys Ile Ser Ile Arg Pro Gly Phe Pro Gln Gln
            20                  25                  30

TCT TCC TGT CTG AGG CTG CAT CCC ATT CGG CAG TTT TCA ATA AGG GCC    144
Ser Ser Cys Leu Arg Leu His Pro Ile Arg Gln Phe Ser Ile Arg Ala
        35                  40                  45

AGG TTT CTG TCA GAT GCC ACA GGA CAA ATG GAG CAC ATA GAA GAC AAA    192
Arg Phe Leu Ser Asp Ala Thr Gly Gln Met Glu His Ile Glu Asp Lys
    50                  55                  60

CAA TAT CCC CAG AAA TGC CAG GAC CCC CTT TTG TCA CAC CTG CAG CCC    240
Gln Tyr Pro Gln Lys Cys Gln Asp Pro Leu Leu Ser His Leu Gln Pro
 65                  70                  75                  80

CCC TCA CCT GGT CAG ACA CAT GGG GGG CTG AAG CGC TAC TAC AGC ATC    288
Pro Ser Pro Gly Gln Thr His Gly Gly Leu Lys Arg Tyr Tyr Ser Ile
                85                  90                  95

TGC CAA GAC ACT GCC TTG AGA CAC CCA AGC TTG GAA GGC GGG GCA GGG    336
Cys Gln Asp Thr Ala Leu Arg His Pro Ser Leu Glu Gly Gly Ala Gly
           100                 105                 110

ATG AGC CCC GTG GAA AGG ACT CGG AAC TCC TTG AGC CCC ACC ATG GCA    384
Met Ser Pro Val Glu Arg Thr Arg Asn Ser Leu Ser Pro Thr Met Ala
       115                 120                 125

CCC AAG CTC AGC TTA GAG GTT CGA AAA CTC AGC AAC GGC AGG TTA TCC    432
Pro Lys Leu Ser Leu Glu Val Arg Lys Leu Ser Asn Gly Arg Leu Ser
   130                 135                 140

ACG TCC CTG AGG CTG GGG CCC CTG CAG CCT CGG GGA GTA CCA CTT CGA    480
Thr Ser Leu Arg Leu Gly Pro Leu Gln Pro Arg Gly Val Pro Leu Arg
```

-continued

| 145 | 150 | 155 | 160 |
|---|---|---|---|

GAG AAG AAG GCC ACC CAG 498
Glu Lys Lys Ala Thr Gln
165

(2) INFORMATION FOR SEQ ID NO:15:

(i) SEQUENCE CHARACTERISTICS:
(A) LENGTH: 69 base pairs
(B) TYPE: nucleic acid
(C) STRANDEDNESS: single
(D) TOPOLOGY: linear (ii) MOLECULE TYPE: DNA (genomic)

(vii) IMMEDIATE SOURCE:
(B) CLONE: D-3 oligonucleotide probe (nucleotides 820- 888)

(ix) FEATURE:
(A) NAME/KEY: CDS
(B) LOCATION: 1..69

(xi) SEQUENCE DESCRIPTION: SEQ ID NO:15:

GAC AGG TAC ACA GCG GTG GTC ATG CCA GTT CAC TAT CAG CAC GGC ACC 48
Asp Arg Tyr Thr Ala Val Val Met Pro Val His Tyr Gln His Gly Thr
1 5 10 15

GGG CAG AGC TCC TGT AGA CGT 69
Gly Gln Ser Ser Cys Arg Arg
20

(2) INFORMATION FOR SEQ ID NO:16:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(vii) IMMEDIATE SOURCE:
(B) CLONE: Variant D-3 pCR amplimer (nucleotides 410- 433)

(xi) SEQUENCE DESCRIPTION: SEQ ID NO:16:

CATTTTGGAG TCGCGTTCCT CTG 23

(2) INFORMATION FOR SEQ ID NO:17:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(vii) IMMEDIATE SOURCE:
(B) CLONE: Variant D-3 pCR amplimer (nucleotides 1800- 1825)

(xi) SEQUENCE DESCRIPTION: SEQ ID NO:17:

CACTCCCTTT ACCCACTTCG AGATGC 26

(2) INFORMATION FOR SEQ ID NO:18:

(i) SEQUENCE CHARACTERISTICS:
(A) LENGTH: 38 amino acids
(B) TYPE: amino acid
(D) TOPOLOGY: linear (ii) MOLECULE TYPE: peptide -continued ( v i i ) IMMEDIATE SOURCE:
( B ) CLONE: Variant D-3 dopaminergic receptor peptide ( x i ) SEQUENCE DESCRIPTION: SEQ ID NO:18:

Met Ala Pro Leu Ser Gln Ile Ser Thr His Leu Asn Ser Thr Cys Gly
1 5 10 15

Ala Glu Asn Ser Thr Gly Val Asn Arg Ala Arg Pro His Ala Tyr Tyr
20 25 30

Ala Leu Ser Tyr Cys Ala
35

( 2 ) INFORMATION FOR SEQ ID NO:19:

( i ) SEQUENCE CHARACTERISTICS:
( A ) LENGTH: 13 amino acids
( B ) TYPE: amino acid
( D ) TOPOLOGY: linear ( i i ) MOLECULE TYPE: peptide ( v i i ) IMMEDIATE SOURCE:
( B ) CLONE: Variant D-3 dopaminergic receptor peptide
( 1 3 5 - 1 4 7 )

( x i ) SEQUENCE DESCRIPTION: SEQ ID NO:19:

Pro Val His Tyr Glu His Gly Thr Gly Gln Ser Ser Cys
1 5 10

( 2 ) INFORMATION FOR SEQ ID NO:20:

( i ) SEQUENCE CHARACTERISTICS:
( A ) LENGTH: 13 amino acids
( B ) TYPE: amino acid
( D ) TOPOLOGY: linear ( i i ) MOLECULE TYPE: peptide ( v i i ) IMMEDIATE SOURCE:
( B ) CLONE: Variant D-3 dopaminergic receptor peptide
( 1 7 5 - 1 8 7 )

( x i ) SEQUENCE DESCRIPTION: SEQ ID NO:20:

Thr Gly Asp Pro Ser Ile Cys Ser Ile Ser Asn Pro Asp
1 5 10

( 2 ) INFORMATION FOR SEQ ID NO:21:

( i ) SEQUENCE CHARACTERISTICS:
( A ) LENGTH: 166 amino acids
( B ) TYPE: amino acid
( D ) TOPOLOGY: linear ( i i ) MOLECULE TYPE: peptide ( v i i ) IMMEDIATE SOURCE:
( B ) CLONE: Variant D-3 dopaminergic receptor peptide ( 2 1 0 - 3 7 5 )

( x i ) SEQUENCE DESCRIPTION: SEQ ID NO:21:

Arg Ile Tyr Ile Val Leu Arg Gln Arg Gln Arg Lys Arg Ile Leu Thr
1 5 10 15

Arg Gln Asn Ser Gln Cys Ile Ser Ile Arg Pro Gly Phe Pro Gln Gln
20 25 30

Ser Ser Cys Leu Arg Leu His Pro Ile Arg Gln Phe Ser Ile Arg Ala
35 40 45

Arg Phe Leu Ser Asp Ala Thr Gly Gln Met Glu His Ile Glu Asp Lys
50 55 60

-continued

```
Gln Tyr Pro Gln Lys Cys Gln Asp Pro Leu Leu Ser His Leu Gln Pro
65                  70                  75                  80

Pro Ser Pro Gly Gln Thr His Gly Gly Leu Lys Arg Tyr Tyr Ser Ile
                85                  90                  95

Cys Gln Asp Thr Ala Leu Arg His Pro Ser Leu Glu Gly Gly Ala Gly
            100                 105                 110

Met Ser Pro Val Glu Arg Thr Arg Asn Ser Leu Ser Pro Thr Met Ala
        115                 120                 125

Pro Lys Leu Ser Leu Glu Val Arg Lys Leu Ser Asn Gly Arg Leu Ser
    130                 135                 140

Thr Ser Leu Arg Leu Gly Pro Leu Gln Pro Arg Gly Val Pro Leu Arg
145                 150                 155                 160

Glu Lys Lys Ala Thr Gln
                165
```

( 2 ) INFORMATION FOR SEQ ID NO:22:

( i ) SEQUENCE CHARACTERISTICS:
( A ) LENGTH: 13 amino acids
( B ) TYPE: amino acid
( D ) TOPOLOGY: linear ( i i ) MOLECULE TYPE: peptide ( v i i ) IMMEDIATE SOURCE:
( B ) CLONE: D-3 dopaminergic receptor peptide (135-147)

( x i ) SEQUENCE DESCRIPTION: SEQ ID NO:22:

```
Pro Val His Tyr Gln His Gly Thr Gly Gln Ser Ser Cys
1               5                   10
```

( 2 ) INFORMATION FOR SEQ ID NO:23:

( i ) SEQUENCE CHARACTERISTICS:
( A ) LENGTH: 293 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: ACC1-ACC1-probe coding for transmembrane ( i x ) FEATURE:
( A ) NAME/KEY: CDS
( B ) LOCATION: 165..293

( x i ) SEQUENCE DESCRIPTION: SEQ ID NO:23:

```
CACTGCCTGC TCTATATAGA AATGTTCCAT CGATATTTGT AGACATGAAA CATTTTAAAC      60

TGTATGTATG TAACATATCC CAGCTCTGAA GAGCCTGATT TAGCCCACAT TGCTGTCTGT     120

CTTTTCCTAG GAACATTTTG GAGTCGCGTT CCTCTGTGTG GGCC ATG GCA CCT CTG      176
                                                 Met Ala Pro Leu
                                                 1

AGC CAG ATA AGC ACC CAC CTC AAC TCC ACC TGC GGG GCA GAA AAC TCC       224
Ser Gln Ile Ser Thr His Leu Asn Ser Thr Cys Gly Ala Glu Asn Ser
  5                  10                  15                  20

ACT GGC GTC AAC CGG GCC CGT CCG CAC GCC TAC TAC GCC CTG TCC TAC       272
Thr Gly Val Asn Arg Ala Arg Pro His Ala Tyr Tyr Ala Leu Ser Tyr
                 25                  30                  35

TGT GCT CTC ATC CTA GCC ATC                                           293
Cys Ala Leu Ile Leu Ala Ile
            40
```

( 2 ) INFORMATION FOR SEQ ID NO:24:

-continued ( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Primer 4

( x i ) SEQUENCE DESCRIPTION: SEQ ID NO:24:

ACATTTTGGA GTCGCGTTCC TCTG 24

( 2 ) INFORMATION FOR SEQ ID NO:25:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Primer 1

( x i ) SEQUENCE DESCRIPTION: SEQ ID NO:25:

CGAATTCATG GCACCTCTGA GCCAGATAAG CAC 33

( 2 ) INFORMATION FOR SEQ ID NO:26:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Primer 2

( x i ) SEQUENCE DESCRIPTION: SEQ ID NO:26:

CGAATTCGAC GAGCACTGTT GCACGATAGC CCGCAGCCA 39

( 2 ) INFORMATION FOR SEQ ID NO:27:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Primer 3

( x i ) SEQUENCE DESCRIPTION: SEQ ID NO:27:

CCACGTCGAC AGATCTCGAA GTGGGTAAAG GGAGTG 36

( 2 ) INFORMATION FOR SEQ ID NO:28:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: Primer 5

-continued ( x i ) SEQUENCE DESCRIPTION: SEQ ID NO:28:

AAGCGCTACT ACAGCATCTG C 21

( 2 ) INFORMATION FOR SEQ ID NO:29:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: pCR oligonucleotide ( x i ) SEQUENCE DESCRIPTION: SEQ ID NO:29:

GATGGTGGGT ATGGGTCAGA AGGA 24

( 2 ) INFORMATION FOR SEQ ID NO:30:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: pCR oligonucleotide ( x i ) SEQUENCE DESCRIPTION: SEQ ID NO:30:

GCTCATTGCC GATAGTGATG ACCT 24

( 2 ) INFORMATION FOR SEQ ID NO:31:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: pCR oligonucleotide ( x i ) SEQUENCE DESCRIPTION: SEQ ID NO:31:

TCCGAATTCT CATTCTACGT GCCCTTCATC 30

( 2 ) INFORMATION FOR SEQ ID NO:32:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: pCR oligonucleotides ( x i ) SEQUENCE DESCRIPTION: SEQ ID NO:32:

GCTTTCTGCG GCTCATCGTC TTAA 24

POLYPEPTIDES HAVING A DOPAMINERGIC RECEPTOR ACTIVITY, NUCLEIC ACIDS CODING FOR THESE POLYPEPTIDES AND USE OF THESE POLYPEPTIDES FOR THE SCREENING OF SUBSTANCES ACTIVE ON THESE POLYPEPTIDES

The object of the invention is polypeptides having a dopaminergic receptor activity and the genes coding for these polypeptides.

The invention also relates to

- vectors containing the genes coding for polypeptides having a dopaminergic receptor activity,
- transformed cells for expressing the above-mentioned genes on which it is possible to evaluate the activity of agonist or antagonist agents towards the said receptors,
- nucleotide probes capable of hybridizing with the genes coding for the above-mentioned polypeptides, probes which should be susceptible of being used for the in vitro diagnosis of diseases, in particular neurological, psychiatric, cardio-vascular or neuroendocrine diseases,
- monoclonal and polyclonal antibodies directed against the above-mentioned polypeptides and which can be used both to purify the said polypeptides and analytically for in vitro diagnosis or therapeutically, in particular in the treatment of diseases involving the dopaminergic systems,
- kits to study the degree of affinity of certain substances for the above-mentioned polypeptides,
- medicines designed more particularly for the treatment of psychiatric, neurological, cardio-vascular or neuroendocrine diseases and containing substances which are active towards the above-mentioned polypeptides having a dopaminergic receptor activity, or containing substances active on cells transfected by the genes or gene fragments coding for the said polypeptides with dopaminergic receptor activity,
- medicines active on the dopaminergic receptors already identified but certain of whose side-effects, attributable to their interaction with the said polypeptides, it would be desirable to diminish.

It has been accepted hitherto that the various effects of dopamine are the result of its interaction with two types of receptors commonly designated by the names of D-1 and D-2 receptors (Kekabian J. W. and Calne D. B., "Multiple receptors for dopamine". Nature, 1979, 277: 93–96). Of the latter, only the sequence of the D-2 receptor was known (Bunzow J. R., Van Tol H. H. M., Grandy D. K., Albert P., Salon J., Christie Mc D., Machida C. A., Neve K. A. and Civelli O. "Cloning and expression of a D-2 dopamine receptor cDNA". Nature, 1988, 336: 783–787) and two isoforms of the D-2 receptor (sometimes designated D-2A and D-2B or also D-2(415) and D-2(444) resulting from the alternative splicing of the messenger RNA of the gene for the said receptor had been described (Giros B., Sokoloff P., Martres M. P., Riou J. F., Emorine L. J. and Schwartz J. C. "Alternative splicing directs the expression of two D-2 dopamine receptor isoforms". Nature, 1989, 342:923–926; Dal Toso R., Sommer B., Ewert M., Herb A., Pritchett D. B., Bach A., Shivers B. D. and Seeburg P. H. "The dopamine D-2 receptor: two molecular forms generated by alternative splicing". The EMBO Journal, 1989, 8:4025–4034).

The D-2 receptor belongs to the family of the receptors containing seven transmembrane domains, coupled to a G protein and exhibiting a certain degree of homology with the receptors of the family of the rhodopsins which are expressed by the photoreceptors of the retina.

The existence of distinct dopaminergic receptors corresponding to the D-1 and D-2 receptors had been suspected by various authors on the basis of indirect observations (see in particular Schwartz J. C., Delandre M., Martres M. P., Sokoloff P., Protais P., Vasse M., Costentin J., Laibe P., Wermuth C. G., Gulat C. and Lafitte A. "Biochemical and behavioral identification of discriminant benzamide derivatives: new tools to differentiate subclasses of dopamine receptors". Catecholamines: neuropharmacology and central nervous system. Theoretical aspects. Alan R. Liss, Inc. N.Y. 1984, pp. 59–72) but had never been proved because the said receptors had never been isolated, nor identified as regards their structure, nor completely defined with respect to their pharmacological properties. In particular, the existence of autoreceptors regulating the synthesis and/or the release of dopamine and/or also the activity of the dopaminergic neurones had been demonstrated but it was commonly accepted that they were identical with the D-2 receptors as far as their pharmacology was concerned.

The object of the invention is to make available novel polypeptides having a dopaminergic receptor activity unrelated to either that of the D-1 dopaminergic receptors or that of the D-2 dopaminergic receptors.

The object of the invention is also screening procedures for novel medicines which act on the novel polypeptides having a dopaminergic receptor action or, on the contrary, whose interaction with the novel polypeptides it is desirable to prevent, and designed, among other purposes, for the treatment of psychiatric, neurological, cardio-vascular or neuroendocrine disorders.

In particular, the novel polypeptide of the invention having a dopaminergic receptor activity:

contains the sequence of 446 amino acids (SEQ ID NO: 2) shown in FIG. 1 or a fragment of that sequence, this fragment being such that either it contains nonetheless the sites contained in that sequence and the presence of which is necessary in order that, when this fragment is present in a membrane, it is capable of binding dopamine to its agonists or antagonists in a specific and measurable manner, for example by means of a radioactive ligand according to the procedure described in Sokoloff P., Martres M. P. and Schwartz J. C. "Three classes of dopamine receptor (D-2, D-3, D-4) identified by binding studies with $^{3}$H-apomorphine and $^{3}$H-domperidone". NaunynSchmiedeberg's Arch. Pharmacol. 1980, 315:89–102 and in Martres M. P., Bouthenet M. L., Sales N., Sokoloff P. and Schwartz J. C. "Widespread distribution of brain dopamine receptors evidenced with $^{125}$I-iodosulpride, a highly selective ligand". Science, 1985, 228: 752–755.

or it is capable of being recognized by antibodies which also recognize the above-mentioned sequence of 446 amino acids (SEQ ID NO:2), but do not recognize either the D-1 dopaminergic receptor or the D-2 dopaminergic receptor, or it is capable of generating antibodies which recognize the above-mentioned sequence of 446 amino acids (SEQ ID NO:2) but do not recognize either the D-1 dopaminergic receptor or the D-2 dopaminergic receptor, or the polypeptide variants which correspond to the polypeptides defined above containing certain localized mutations without the polypeptides losing the properties of a dopaminergic receptor.

In particular, an advantageous variant polypeptide of the invention having a dopaminergic receptor activity:

contains the sequence of 446 amino acids (SEQ. ID. NO: 3) shown in FIG. 2 or a fragment of that sequence, this fragment being such that either it contains nonetheless the sites contained in that sequence and whose presence is necessary in order that, when this fragment is present in a membrane, it is capable of binding dopamine to its agonists or antagonists in a specific and measurable manner, for example by means of a radioactive ligand according to the procedure described in Martres, M. P., Bouthenet, M. L. Salés, N., Sokoloff, P. and Schwartz, J. C. Science 228, 752–755 (1985), or is capable of being recognized by antibodies which also recognize the above-mentioned sequence of 446 amino acids (SEQ. ID. NO:3) but do not recognize either the D-1 dopaminergic receptor or the D-2 dopaminergic receptor, or is capable of generating antibodies which recognize the above-mentioned sequence of 446 amino acids (SEQ. ID. NO: 3) but do not recognize either the D-1 dopaminergic receptor or the D-2 dopaminergic receptor.

The recognition of one of the above-mentioned sequences of 446 amino acids by the above-mentioned antibodies—or the above-mentioned fragment by the above-mentioned antibodies—signifies that the above-mentioned sequence forms a complex with one of the above-mentioned antibodies.

The formation of the antigen (i.e. the sequence of 446 amino acids or the above-mentioned fragment)-antibody complex and the detection of the existence of the complex formed may be made by standard techniques (such as those using a tracer labelled with radioactive isotopes or an enzyme).

As for the definition of the "fragments containing the sites" and compliance with the above-mentioned definition, these will be referred to in the subsequent description.

Among the fragments defined above, the fragment(s) produced by alternative splicing of the messenger RNA produced by the gene coding for one of the two sequences of 446 amino acids defined above is/are preferred.

Advantageously, the polypeptides of the invention correspond to fragments of the sequence shown in FIG. 2 (SEQ ID NO:3), which contain the amino acid corresponding to that at position 139.

Useful polypeptides of the invention are such that they contain the sites contained in one of the above-mentioned sequences of 446 amino acids, the presence of which is necessary in order that, when these polypeptides are exposed at the surface of a cell in the presence of $^{125}$I-iodosulpride, and in the presence of an agonist, the respective affinity of the following agonists: quinpirole, apomorphine, dopamine, for the polypeptides of the invention is in the following order:

the affinity of quinpirole for the polypeptides of the invention is higher than the affinity of apomorphine for the polypeptides of the invention, the affinity of apomorphine for the polypeptides of the invention is approximately equal to the affinity of dopamine for the polypeptides of the invention.

Useful peptides of the invention are those which contain the sites contained in one of the above-mentioned sequences of 446 amino acids, the presence of which is necessary in order that, when these polypeptides are exposed at the surface of a cell in the presence of $^{125}$I-iodosulpride, and in the presence of an antagonist, the respective affinity of the following antagonists: raclopride, UH 232, haloperidol for the polypeptides of the invention is in the following order:

the affinity of raclopride for the peptides of the invention is higher than the affinity of UH 232 for the polypeptides of the invention, and the affinity of UH 232 for the polypeptides of the invention is approximately equal to the affinity of haloperidol for the polypeptides of the invention.

UH 232 is defined in the article by Svensson K. et al. "(+)-AJ 76 and (+)-UH 232: central stimulants acting as preferential dopamine autoreceptor antagonists". Naunyn-Schmiedeberg's Arch. Pharmacol., 1986, 334, 234–245.

In the foregoing and in what follows, a ligand is considered as "agonist" or "antagonist", with reference to the known behaviour of this ligand towards the D-2 receptor.

The measurement of the affinity of an agonist or an antagonist towards the polypeptides of the invention is done by competition between the agonist or antagonist (whose affinity it is desired to measure) and $^{125}$I-iodosulpride, which is a ligand with high affinity for the polypeptide of the invention.

As far as the measurement of the affinity of the agonists or antagonists towards the polypeptides of the invention is concerned, it may be made under the following conditions:

A solution (final volume=400 μl) of 50 mM Tris-HCl buffer is used containing 120 mM NaCl, 5 mM KCl, 2 mM $CaCl_2$, 2 mM $MgCl_2$, 0.1% ascorbic acid, 10 μM 8-hydroxyquinoline, 0.1% bovine serum albumin and 0.1 to 0.2 nM $^{125}$I-iodosulpride, 5 μg of membrane proteins derived from transfected CHO cells in which the polypeptides are present at a concentration of about 1 pmol/mg of membrane protein.

The invention also relates to chimeric proteins in which the polypeptide as defined above or parts of the latter are combined to give a chain of amino acids heterologous with respect to this peptide.

The chimeric polypeptides and proteins of the invention may be glycosylated and may or may not contain disulfide bridges.

For the purposes of simplification, in the remainder of the description, the polypeptides of the invention will be designated as "D-3 receptors".

An advantageous D-3 receptor of the invention is constituted by the amino acid sequence 1 to 446 shown in FIG. 1 (SEQ ID NO:2) or by the amino acid sequence 1 to 446 (SEQ ID NO:3) shown in FIG. 2.

This D-3 receptor is considered to contain seven hydrophobic transmembranar regions separated by intra- and extra-cellular hydrophilic loops.

The invention also relates to the variant polypeptides which correspond to the polypeptides defined above containing certain localized mutations without the polypeptides losing the properties of a dopaminergic D-3 receptor, and which are recognized by antibodies recognizing the transmembranar regions, as well as those which are recognized by antibodies recognizing the regions other than the transmembranar regions.

The invention also relates to nucleic acids which contain or which are constituted by a chain of nucleotides coding for any one of the D-3 receptors previously defined.

More particularly, the invention relates to the nucleic acid which includes the chain of nucleotides shown in FIG. 3 (SEQ ID NO:4), extending from the end constituted by the nucleotide at position 1 to that constituted by the nucleotide at position 1863.

More particularly, the invention also relates to the nucleic acid which includes the chain of nucleotides represented in FIG. 4 (SEQ ID NO:5), extending from the end constituted by the nucleotide at position 1 to that constituted by the nucleotide at position 1863.

The invention relates particularly to the nucleic acid shown in FIG. 2 including or being constituted by the nucleotide chain extending from the end constituted by the nucleotide at position 442 to that constituted by the nucleotide at position 1779 (SEQ ID NO:6).

The nucleic acid defined above corresponds to the part coding for the gene corresponding to the polypeptide shown in FIG. 1 (SEQ ID. NO: 2).

The invention relates particularly to the nucleic acid shown in FIG. 4 including or being constituted by the nucleotide chain extending from the end constituted by the nucleotide at position 442 to that constituted by the nucleotide at position 1779 (SEQ ID NO:7).

The nucleic acid defined above corresponds to the part coding for the gene corresponding to the polypeptide shown in FIG. 2 (SEQ ID NO:3).

The nucleic acids of the invention are preferably such that they correspond to fragments of the chain of nucleotides shown in FIG. 4 and contain the nucleotides corresponding respectively to those situated at the positions 856, 857 and 859 (SEQ ID NO:5).

Also forming part of the invention are the nucleic acids differing from those defined above and which contain certain localized mutations to the extent that these variant nucleic acids can hybridize with the nucleic acids previously defined or with the nucleic acid probes defined hereafter under the conditions of hybridization defined hereafter in the description.

The nucleic acids of the invention may be prepared either by a chemical procedure, or by other procedures.

A suitable method of preparation of the nucleic acids of the invention (containing maximally 200 nucleotides—or bp, in the case of double-stranded nucleic acids) by the chemical route consists of the following steps:

- the synthesis of DNA by using the automated $\beta$-cyanoethyl phosphoramidite method described in Bioorganic Chemistry 4: 274–325, 1986,
- the cloning of the DNAs thus obtained in a suitable plasmid vector and the recovery of the DNAs by hybridization with a suitable probe.

A method of preparation of nucleic acids longer than 200 nucleotides—or bp (in the case of double-stranded nucleic acids) by the chemical route consists of the following steps:

- the assembly of the chemically synthesized oligonucleotides, provided at their ends with various restriction sites, the sequences of which are compatible with the amino acid sequence of the natural polypeptide according to the principle described in Proc. Nat. Acad. Sci. USA 80; 7461–7465, 1983,
- the cloning of the DNAs thus obtained in an appropriate plasmid vector and the recovery of the desired nucleic acid by hybridization with a suitable probe.

Another procedure for the preparation of the nucleic acids of the invention starting from mRNA consists of the following steps:

- preparation of cellular RNA from any tissue expressing the D-3 dopaminergic receptor according to the procedures described by Maniatis et al., "Molecular cloning", Cold Spring Harbor Laboratory, 1982, and Ausubel F. M., Brent R., Kingston R. E., Moore D. D., Smith J. A., Seidman J. G. and Struhl K. (1989) Current Protocols in Molecular Biology, chapter 4, Green Publishing Associates and Wiley-Interscience, New York,
- recovery and purificaton of the mRNAs by chromatography of the total cellular RNAs through a column of immobilized oligo dT,
- synthesis of a cDNA strand starting from the purified mRNAs according to the procedure described in Gene 25:263, 1983,
- cloning of the nucleic acids thus obtained in a suitable plasmid vector and recovery of the desired nucleotide sequence by using a suitable hybridization probe.

In order to prepare the nucleic acids of the invention, the chemically synthesized oligonucleotide hybridization probes may be the following:

- that defined by the nucleic acid sequence shown in FIG. 3, extending from the end constituted by the nucleotide at position 1 to that constituted by the nucleotide at position 441 (SEQ ID NO:8),
- that defined by the nucleic acid sequence shown in FIG. 3, extending from the end constituted by the nucleotide at position 442 to that constituted by the nucleotide at position 537 (SEQ ID NO:9),
- that defined by the nucleotide sequence shown in FIG. 3, extending from the end constituted by the nucleotide at position 718 to that constituted by the nucleotide at position 753 (SEQ ID NO:10),
- that defined by the nucleic acid sequence shown in FIG. 3, extending from the end constituted by the nucleotide at position 820 to that constituted by the nucleotide at position 888 (SEQ ID NO:11),
- that defined by the nucleic acid sequence shown in FIG. 3, extending from the end constituted by the nucleotide at position 958 to that constituted by the nucleotide at position 996 (SEQ ID NO:12),
- that defined by the nucleic acid sequence shown in FIG. 3, extending from the end constituted by the nucleotide at position 1068 to that constituted by the nucleotide at position 1240 (SEQ ID NO:13),
- that defined by the nucleic acid sequence shown in FIG. 3, extending from the end constituted by the nucleotide at position 1068 to that constituted by the nucleotide at position 1566 (SEQ ID NO:14), or their complementary nucleotide sequence;

these are sequences which have been derived from those of FIG. 3 and they may be used under the hybridization conditions described by Maniatis et al., "Molecular cloning", Cold Spring Harbor Laboratory, 1982.

In order to prepare the nucleic acids of the invention, another chemically synthesized oligonucleotide hybridization probe may be the following:

- that defined by the nucleic acid sequence shown in FIG. 4, extending from the end constituted by the nucleotide at position 820 to that constituted by the nucleotide at position 888 (SEQ ID NO:15).

This sequence is derived from the sequences of FIG. 4 and it may be used under the hybridization conditions described by Maniatis et al. (1982) already mentioned.

The synthesis of the cDNA strand and its subsequent in vitro amplification may also be carried out by using the PCR (Polymerase Chain Reaction) method, as described for example by Goblet et al., Nucleic Acid Research, 17, 2144, 1989 "One step amplification of transcripts in total RNA using Polymerase Chain Reaction", by using two defined chemically synthesized amplimers starting from the sequence shown in FIG. 3. Appropriate amplimers are for example: that defined in FIG. 3 from nucleotide 410 to nucleotide 433 (SEQ ID NO:16) and that defined in FIG. 3 from nucleotide 1800 to nucleotide 1825 (SEQ ID NO:17).

The nucleic acid fragment amplified may then be cloned according to the procedures described in Ausubel F. M., Brent R., Kingston R. E., Moore D. D., Smith J. A., Seidman J. G. and Struhl K. (1989) Current Protocols in Molecular Biology, chapter 3, Green Publishing Associates and Wiley-Interscience, New York.

The invention also relates to the recombinant vectors, in particular for the cloning and/or expression, in particular of the plasmid, cosmid, phage or virus type, containing a nucleic acid of the invention at one of its sites inessential for its replication.

An appropriate vector of the invention contains at one of its sites inessential for its replication elements necessary for promoting the expression of a polypeptide according to the invention in a cell host and, if necessary, a promoter recognized by the polymerases of the cell host, in particular an inducible promoter and possibly a signal sequence and an anchoring sequence.

The invention also relates to a cell host transformed by a recombinant vector defined previously containing the regulatory elements making possible the expression of the nucleotide sequence coding for one of the polypeptides according to the invention in this host.

By cell host is meant any organism capable of being maintained in culture.

One of the microorganisms used may be constituted by a bacterium, in particular *Escherichia coli.*

An organism of choice is constituted by a eukaryotic organism such as CHO cells (Chinese Hamster Ovary) or COS-7 (kidney fibroblasts of the African green monkey transformed by the SV-40 virus).

However, other organisms may be used just as readily, provided of course that vectors, in particular plasmid vectors capable of replicating in them are available as well as nucleotide sequences which can be inserted into these vectors and which are capable, when they are followed in these vectors by an insert coding for a polypeptide of the invention, of ensuring the expression of this insert in the selected organisms and its transport into the membranes of these cell hosts.

The invention also relates to the antibodies directed specifically against one of the polypeptides of the invention, these antibodies being such that they do not recognize either the D-1 dopaminergic receptor or the D-2 dopaminergic receptor. In particular, these antibodies recognize the following amino acid sequences:

- that defined by the sequence of amino acids shown in FIG. 1 extending from the extremity constituted by the amino acid at position 1 to that constituted by the amino acid at position 38 (SEQ ID NO:13),
- that defined by the amino acid sequence shown in FIG. 1 extending from the extremity constituted by the amino acid at position 135 to that constituted by the amino acid at position 147 (SEQ ID NO:19),
- that defined by the amino acid sequence shown in FIG. 1 extending from the extremity constituted by the amino acid at position 175 to that constituted by the amino acid at position 187 (SEQ ID NO:20),
- that defined by the amino acid sequence shown in FIG. 1 extending from the extremity constituted by the amino acid at position 210 to that constituted by the amino acid at position 375 (SEQ ID NO:21),
- that defined by the amino acid sequence shown in FIG. 2 extending from the extremity constituted by the amino acid at position 135 to that constituted by the amino acid at position 147 (SEQ ID NO:22).

In order to obtain the antibodies, one of the above-mentioned polypeptides may be injected into an animal.

Monoclonal antibodies are prepared by cell fusion between myeloma cells and spleen cells of immunized mice, according to the standard procedures.

The antibodies of the invention can be used in vitro to diagnose whether certain cells have tumoral character or not and whether certain tumors are benign or malignant, to the extent to which these elements are correlated with the pathological expression of the D-3 receptor.

In fact, it has been possible to observe that in certain tumors, in particular tumors of the lung, it is possible to detect the expression of dopaminergic receptors which normally ought not to be present (Sokoloff P., Riou J. F., Martres M. P. and Schwartz J. C. "Presence of D-2 dopamine receptors in human tumoral cell lines". Biochemm. Biophys. Res. Comm. 1989, 162: 575–582).

This in vitro diagnosis starting from a biological sample likely to contain the D-3 dopaminergic receptor comprises:

- the placing in contact of an antibody of the invention with the above-mentioned biological sample under conditions leading to the possible production of an immunological complex formed between the D-3 dopaminergic receptor or a product which is derived from it and the antibody of the invention,
- the detection of the above-mentioned immunological complex formed.

The invention also relates to the synthetic or natural nucleotide probes which hybridize with one of the nucleic acids defined above or with their complementary sequences or the corresponding RNA, these probes being such that they do not hybridize with either the gene or the messenger RNAs of the D-1 and D-2 dopaminergic receptors.

The probes of the invention contain a minimum of 10, and advantageously 15 nucleotides and may comprise maximally the entire nucleotide sequence shown in FIG. 3 or in FIG. 4.

In the case of the shortest probes, i.e. those of about 10 to about 100 nucleotides, suitable hybridization conditions are the following:

900 mM of NaCl, 90 mM of tri-sodium citrate pH 7.0, 100 $\mu$g/ml of salmon sperm DNA, 0.05% of sodium pyrophosphate, 10 to 25% deionized formamide, 0.02% of Ficoll (MW 400,000), 0.02% of bovine serum albumin, 0.02% of polyvinylpyrrolidone, for 14 to 16 hours at 42° C.

In the case of the longest probes, i.e. containing more than about 100 nucleotides, suitable hybridization conditions are the following:

600 mM of NaCl, 60 mM of tri-sodium citrate, 20 μg/ml of salmon sperm DNA, 20 μg/ml of yeast tRNA, 8 mM of Tris-HCl pH 7.4, 40 to 60% of deionized formamide, 0.02% of Ficoll, 0.02% of bovine serum albumin, 0.02% of polyvinylpyrrolidone, 0.2% of sodium dodecyl sulfate, 10% of dextran sulfate.

The invention relates in particular to the nucleotide probes previously defined.

The probes of the invention may be used as diagnostic tools, in particular in vitro, for neurological, psychiatric and cardio-vascular diseases.

The probes of the invention may also be used to study in detail the alternative splicing of the messenger RNA produced by the gene coding for the sequence of 446 amino acids defined above, since the existence or non-existence of this splicing may be linked to neurological, psychiatric, cardio-vascular or neuroendocrinine diseases.

More particularly, the probes of the invention may be used to detect genetic anomalies, in particular polymorphisms or point mutations.

As far as the detection of polymorphisms of the gene coding for the D-3 dopaminergic receptor in an individual is concerned, it may be carried out starting from a biological sample such as blood, taken from an individual according to a procedure comprising the following steps:

- the treatment of the nucleic acid derived from the biological sample mentioned above with the aid of a restriction enzyme under conditions making possible the production of restriction fragments resulting from the cleavage of the said nucleic acid at those restriction sites recognized by the said enzyme,
- the placing in contact of a nucleotide probe of the invention capable of hybridizing with the above-mentioned fragments under conditions leading to the possible production of hybridization complexes between the said probe and the above-mentioned restriction fragments,
- the detection of the above-mentioned hybridization complexes,
- the measurement of the size of possible polymorphic restriction fragments incorporated in the above-mentioned hybridization complexes.

As regards the in vitro diagnostic method for the detection of point mutations in the nucleic acid or in a fragment of the nucleic acid coding for the D-3 dopaminergic receptor in an individual, it may be carried out according to the procedure comprising the following steps:

- the placing in contact of a nucleotide probe of the invention with a biological sample, for example blood, under conditions leading to the possible production of a hybridization complex formed between the probe and the nucleic acid or a fragment of the nucleic acid mentioned above,
- the detection of the above-mentioned hybridization complex,
- the sequencing of the nucleic acid or the fragment of the nucleic acid incorporated into the above-mentioned hybridization complex,
- the comparison of the sequence of the nucleic acid or the fragment of nucleic acid incorporated into the above-mentioned hybridization complex with the sequence of the nucleic acid (not exhibiting mutations) or the fragment of the nucleic acid (not exhibiting mutations) coding for the D-3 dopaminergic receptor.

As far as the detection of the alternative splicing of the messenger RNA produced by the gene coding for the D-3 receptor is concerned, it may be carried out by quantification of the messenger RNA contained in a sample of tissue by using one of the probes of the invention.

The probes of the invention may also be used to detect the pathological expression of the D-3 dopaminergic receptor, this expression being revealed by the presence of messenger RNA of the D-3 dopaminergic receptor in cells in which it ought not to be present.

This in vitro detection may be carried out starting from a biological sample such as blood taken from an individual, according to a procedure which comprises the following steps:

- the possible prior amplification of the quantities of the nucleotide sequence likely to be contained in a biological sample taken from a patient, by means of a DNA primer,
- the placing in contact of the biological sample mentioned above with a nucleotide probe under conditions leading to the production of a hybridization complex formed from the said probe and the said nucleotide sequence,
- the detection of the above hybridization complex which has been able to form.

This pathological expression of the D-3 dopaminergic receptor may be manifest in the case of certain tumors, and may also be correlated with the malignant or benign character of certain tumors.

The polypeptides of the invention may be prepared by culture in a suitable medium of a cell host transformed beforehand by a recombinant vector containing one of the nucleic acids previously defined and by recovery from the above-mentioned culture of the polypeptide produced by the said transformed cell host.

Another procedure for the preparation of the polypeptides of the invention is characterized in that, starting preferably from the C-terminal amino acid, the successive amino acid residues are condensed one at a time in the required order, or amino acid residues are condensed with previously formed fragments already containing several amino acid residues in the correct order, or also several fragments previously formed in this manner are condensed with each other, it being understood that care will be taken to protect beforehand all of the reactive functions borne by these amino acid residues or fragments with the exception of the amine function of the one and the carboxyl function of the other which must normally participate in the formation of the peptide bonds, in particular after activation of the carboxyl function according to the known methods used in the synthesis of peptides and this is continued in a stepwise manner until the N-terminal amino acid is reached.

In order to bring about the expression of the D-3 dopaminergic receptors in a bacterium such as *E. coli* or in a eucaryotic cell such as a CHO cell, the following steps are carried out:

- the transformation of a competent cell host with a vector, in particular a plasmid or phage, in which a sequence of nucleotides coding for the D-3 receptor (insert) has previously been inserted, under the control of regulatory elements, in particular a promoter recognized by the polymerases of the cell host and making possible the expression of the said sequence of nucleotides in the cell host used, the culture of the transformed cell host under conditions which permit the expression of the said insert, and the transport of the D-3 receptor expressed towards the membrane in a manner such that the transmembranar sequences of the D-3 receptor are exposed at the surface of the transformed cell host.

In the case of expression in eukaryotic cells, the regulatory elements may include the endogenous promoter of the dopaminergic receptors or viral promoters such as those of the SV40 virus or the Rous sarcoma virus (RSV).

In the case of expression in *E. coli,* the regulatory elements may include the promoter of the lactose operon or of the tryptophan operon.

The invention also relates to a procedure for the detection of the capacity of a dopaminergic molecule to behave as a ligand with respect to a polypeptide of the invention. This procedure comprises:

the placing in contact of the dopaminergic molecule with a cell host transformed beforehand by a vector itself modified by an insert coding for the above-mentioned polypeptide, this host bearing at its surface one or more specific sites of this polypeptide, where appropriate after induction of the expression of this insert, this placing in contact being performed under conditions leading to the formation of a bond between at least one of these specific sites and the said molecule provided that the latter has proved to effectively possess an affinity for this polypeptide, the detection of the possible formation of a complex of the ligand-polypeptide type.

The invention also relates to a procedure for the study of the affinity of a polypeptide of the invention for one or several specific ligands. This procedure comprises:

the transformation of a competent cell host with a vector, in particular a plasmid or a phage, into which has been inserted beforehand a sequence of nucleotides coding for the D-3 receptor (insert), under the control of regulatory elements, in particular a promoter recognized by the polymerases of the cell host and making possible the expression of the said sequence of nucleotides in the cell host used, the culture of the transformed cell host under conditions permitting the expression of the said insert, and the transport of the D-3 receptor expressed towards the membrane in a manner such that the transmembranar sequences of the D-3 receptor are exposed at the surface of the transformed cell host, the placing in contact of the cell host with these specific ligands, the detection of a specific bond between the said transformed cell host and the said specific ligands.

The procedure described above also makes possible the identification of the "fragments containing the sites", a matter already referred to, and which comprise only a part of the sequence of 446 amino acids shown in FIG. 1 (SEQ ID NO:2) or FIG. 2 (SEQ ID NO:3).

This identification consists of using inserts shorter than the nucleic acid coding for the above-mentioned sequence, of carrying out the steps relating to the expression, the transport of the expression product and its exposure noted above. Once the expression, the transport of the expression product and its exposure on the membrane have been obtained, as well as the reaction with the ligands as previously defined, it is then possible to define the fragments containing the essential sites. Consequently, the absence of reaction with the ligands, as previously defined, by using fragments shorter than the complete sequence would tend to show that certain essential sites have been eliminated.

The invention also relates to a kit for the detection of the possible affinity of a ligand for a polypeptide of the invention. This kit contains:

a culture of cell hosts transformed by a modified vector such as previously defined or a culture of cell hosts previously defined, or a preparation of membranes of the said hosts, physical or chemical agents to induce the expression of the nucleotide sequence contained in the modified vector when the promoter placed upstream from this sequence is a promoter inducible by the said physical or chemical agents, and to produce a protein, one or more control ligands having specific affinities for the above-mentioned polypeptide, physical or chemical agents for the characterization of the biological activity of the protein expressed.

The invention also relates to a procedure for the screening of medicines designed for the treatment of neurological (such as Parkinson's disease), psychiatric (such as psychotic states), cardiovascular (such as arterial hypertension) or neuroendocrine (such as the dysfunction of the hypothalamo-hypophyseal axis) diseases.

The invention also relates to medicines containing as active ingredient a substance active on at least one of the polypeptides according to the invention having a dopaminergic receptor activity or containing as active ingredient substances active on cells transfected by the genes or the fragments of genes coding for at least one of the polypeptides with a dopaminergic receptor activity according to the invention, in combination with a pharmaceutically acceptable vehicle.

The invention also relates to medicines containing as active ingredient a substance active on the D-1 or D-2 dopaminergic receptors, but inactive on the polypeptides with a dopaminergic receptor activity according to the invention.

The invention also relates to a procedure for the measurement of the affinity of ligands towards a polypeptide of the invention with the aid of a ligand labelled by means of a radioisotopic and selective method with respect to the above-mentioned polypeptide of the invention, comprising the following steps:

if necessary, the determination of the above-mentioned ligand which is selective with respect to the above-mentioned polypeptide according to the procedure described relating to the study of the affinity of a polypeptide of the invention for one or more specific ligands, the labelling of the selective ligand thus defined by a radioisotopic procedure, the placing in contact, according to the procedure described in Martres, M. P., Bouthenet, M. L., Sales, N., Sokoloff, P. and Schwartz, J. C. Science 228, 752–755 (1985), of biological membranes, in particular of brain, containing the above-mentioned polypeptide of the invention, with the labelled selective ligand and a ligand whose affinity it is desired to measure, the detection of the possible formation of a complex of the polypeptide-labelled selective ligand type.

It is also possible to work with kidney membranes as the biological membrane in question.

The labelled ligand which is selective towards a polypeptide of the invention may also be labelled by means of an enzymatic method.

As far as the detection of the complex of the polypeptide-labelled selective ligand type is concerned, it may be performed according to standard procedures.

The invention also relates to a procedure for the selective labelling of a polypeptide of the invention with the aid of a ligand labelled according to a radioisotopic procedure on biological membranes containing, on the one hand, the D-1 and/or D-2 receptor and, on the other, the above-mentioned polypeptide, comprising the following steps:

- if necessary, the determination of a ligand selective with respect to the D-1 and/or D-2 receptor according to the procedure described relating to the study of the affinity of a polypeptide of the invention,
- the placing in contact, according to the procedure described in Martres, M. P., Bouthenet, M. L. Sales, N., Sokoloff, P. and Schwartz, J. C. Science 228, 752–755 (1985), of the above-mentioned biological membranes with the above-mentioned ligand selective with respect to the D-1 and D-2 receptor and with a ligand labelled according to a radioisotopic procedure, in particular $^{125}$I-iodosulpride, which leads to the selective labelling of the above-mentioned polypeptide, the D-1 and/or D-2 receptor being occupied by the above-mentioned selective ligand,
- the detection of the formation of the complex of the polypeptide-labelled ligand type.

The detection of the complex of the polypeptide-labelled ligand type may be performed by standard techniques.

The labelled ligand may also be labelled according to an enzymatic method.

This procedure is based on the use of a labelled ligand (labelled by a radioisotopic or enzymatic procedure), a ligand which is not selective with respect to the D-3 receptor, which implies that if the D-1 and/or D-2 receptors are also present in the above-mentioned biological membranes, this labelled ligand is capable of binding simultaneously to the D-1, D-2 and D-3 receptors.

In order to use the labelled ligand under conditions such that the labelling of the D-3 receptor is selective, recourse is had to a ligand selective with respect to the D-2 and/or D-1 receptor. The purpose of this is to occupy the D-2 and/or D-1 receptor(s) and make it (them) unavailable to the above-mentioned labelled ligand. Hence, the result is that the above-mentioned labelled ligand is able to occupy only the D-3 receptor, which leads to the formation of a complex of the labelled ligand-D-3 receptor type.

The D-3 receptor exhibits an anatomical distribution and pharmacological characteristics which distinguish it from the D-1 and D-2 receptors. It is preferentially expressed in the limbic regions of the brain implicated in cognitive and emotional processes whereas the D-1 and D-2 receptors are present in most of the dopaminoceptive regions, in particular the extrapyramidal system implicated in involuntary motoricity.

The very special anatomical location of the D-3 receptor in the limbic system suggests that selective agonists of this receptor could have therapeutic effects on certain cognitive and emotional disorders associated with Parkinson's disease.

The neuroleptics used in the clinic to treat schizophrenias all have an affinity for the D-3 receptor of the order of 1 to 10 nM which suggests that the blockade of this receptor is probably implicated in the therapeutic effects of the neuroleptics. Furthermore, the ratio of the respective affinities of the neuroleptics for the D-2 and D-3 receptors is expressed by the ratio $K_iD-2/K_iD-3$ as indicated in Table I below.

TABLE 1

Pharmacology of the D-2 and D-3 receptors expressed in CHO cells.

| | $K_i$ Value (nM) | | Ratio |
|---|---|---|---|
| Agents | D-2 receptor | D-3 receptor | $\frac{K_{iD2}}{K_{iD3}}$ |
| Agonists | | | |
| Bromocriptine | 5.3 ± 0.6 | 7.4 ± 1.3 | 0.7 |
| Apomorphine | 24 ± 2 | 20 ± 3 | 1.2 |
| SKF 38393 | 9,560 ± 408 | 5,000 ± 500 | 1.9 |
| Dopamine | 474 ± 33 | 25 ± 3 | 19 |
| Dopamine + Gpp(NH)p | 1,705 ± 270 | 27 ± 3 | 63 |
| TL 99 | 18 ± 1 | 0.91 ± 0.08 | 20 |
| Pergolide | 21 ± 3 | 0.62 ± 0.04 | 33 |
| Quinpirole | 576 ± 47 | 5.1 ± 0.3 | 113 |
| Antagonists | | | |
| Domperidone | 0.30 ± 0.03 | 9.5 ± 0.5 | 0.032 |
| Haloperidol | 0.45 ± 0.03 | 9.8 ± 0.3 | 0.046 |
| Spiperone | 0.069 ± 0.002 | 0.61 ± 0.05 | 0.11 |
| Thioproperazine | 0.21 ± 0.01 | 1.7 ± 0.1 | 0.12 |
| Prochlorperazine | 4.7 ± 0.4 | 35 ± 3 | 0.13 |
| (+)Sulpiride | 85 ± 7 | 422 ± 19 | 0.20 |
| Clozapine | 56 ± 2 | 180 ± 17 | 0.31 |
| (−)Sulpiride | 9.2 ± 0.3 | 25 ± 1 | 0.36 |
| Thioridazine | 3.3 ± 0.2 | 7.9 ± 0.8 | 0.42 |
| Anisulpride | 1.7 ± 0.1 | 3.8 ± 0.3 | 0.45 |
| Chlorpromazine | 2.8 ± 0.2 | 6.1 ± 0.3 | 0.46 |
| Raclopride | 1.8 ± 0.1 | 3.5 ± 0.3 | 0.51 |
| Iodosulpride* | 0.61 ± 0.05* | 1.2 ± 0.2* | 0.52 |
| Pimozide | 2.4 ± 0.3 | 3.7 ± 0.5 | 0.65 |
| (+)AJ 76 | 270 ± 14 | 91 ± 5 | 3.0 |
| (+)UH 232 | 40 ± 1 | 9.2 ± 0.1 | 4.4 |

The values of $K_i$ are derived from experiments described in the legend to FIGS. 5*a* and 5*b*. The curves were analysed by the method of non-linear regression using a calculator (Martres M. P. et al. "Selection of dopamine antagonists discriminating various behavioural responses and radioligand binding sites" Naunyn-Schmiedeberg's Arch. Pharmacol., 1984, 325: 102–115). The values of $*K_D$ result from saturation kinetics at equilibrium. The mean values ± the standard deviation correspond to 2–3 experiments, with similar results. The terms agonists and antagonists refer to the actions of the medicines on the D-2 receptors. The compounds are ranged according to their $K_iD-2/K_iD-3$ ratio.

SKF 38393 is described in Pendleton R. G. et al. "Studies on renal dopamine receptors with SKF 38393, a new agonist" Eur. J. Pharmacol., 1978, 51: 19–28, AJ 76 and UH 232 are described in Svensson K. et al.

"(+)-AJ 76 and (+)-UH 232: central stimulants acting as preferential dopamine autoreceptor antagonists" Naunyn-Schmiedeberg's Arch. Pharmacol., 1986, 334: 234–245.

TL99 is described in Goodale D. B. et al. Neurochemical and behavioral evidence for a selective presynaptic dopamine receptor agonist. Science, 1980, 210, 1141–1143.

This ratio is correlated with certain clinical properties of the neuroleptics: those which possess a low ratio, of about 0.05 to about 0.13 (haloperidol, thioproperа- zine, prochlorperazine) are neuroleptics for which the incidence of side effects (parkinsonism, dystonia and tardive dyskinesias) is the highest whereas those with the highest ratio, of about 0.3 to about 0.6 (clozapine, amisulpride, thioridazine, sulpiride) are "atypical" neuroleptics which cause fewer side effects and/or have disinhibitory properties in certain deficiency forms of schizophrenia.

The screening of potential neuroleptics by comparison of their respective affinities for the D-2 and D-3 receptors thus provide a predictive test of their "atypical" properties which has hitherto not been available.

Other characteristics and advantages of the invention will become apparent in the remainder of the description and the examples, in particular in relation with the drawings and tables in which:

BRIEF DESCRIPTION OF THE DRAWINGS

FIGS. 1A and B present the amino acid sequences of the D-2 dopaminergic receptor (second line) (SEQ ID NO:1) of the rat, aligned with that of a variant of the D-3 dopaminergic receptor of the rat (first line) (SEQ ID NO:2). In the sequences of the D-2 dopaminergic receptor, the amino acid residues which are identical and in the same position as those of the variant of the D-3 dopaminergic receptor are marked by double lines (=).

In order to demonstrate the homologies, deletions have been introduced into the two sequences, and these deletions are represented by dashes (—).

In the extra-cellular N-terminal region of the variant of the D-3 receptor, the consensus sequences for the sites of glycosylation linked to asparagine (NXS/T) are in positions 12 and 19.

FIGS. 2A and B present the amino acid sequences of the D-2 dopaminergic receptor (second line) (SEQ ID NO:1) of the rat aligned with that of the D-3 dopaminergic receptor of the rat (first line) (SEQ ID NO:3) according to Bunzow J. R. et al. ("Cloning and expression of a rat D-2 dopamine receptor cDNA", Nature, 1988, 336: 783–787).

The transmembranar regions are shown in boxes and the positions of the introns for the D-2A receptor of the rat (20, 22, 30, 33) and the D-3 receptor, deduced from the analysis of λRGE 12A and λRGS 3, are indicated by arrows. Each "equal" sign indicates the conservation of an amino acid and the "dashes" correspond to conservative substitutions in which the groups are (H,K,R), (I,L,V,M), (A,G,S,T), (Y,F,W), (D,E,P,N,B,Z), (P) and (C).

FIGS. 3A to D present the nucleic acid sequence of the above-mentioned variant (cf. FIGS. 1A and B) of the D-3 dopaminergic receptor of the rat, and the corresponding amino acid sequence (SEQ ID NO:4).

FIGS. 4A to D present the nucleic acid sequence of the D-3 dopaminergic receptor of the rat, and the corresponding amino acid sequence (SEQ ID NO:5).

Figure 5:
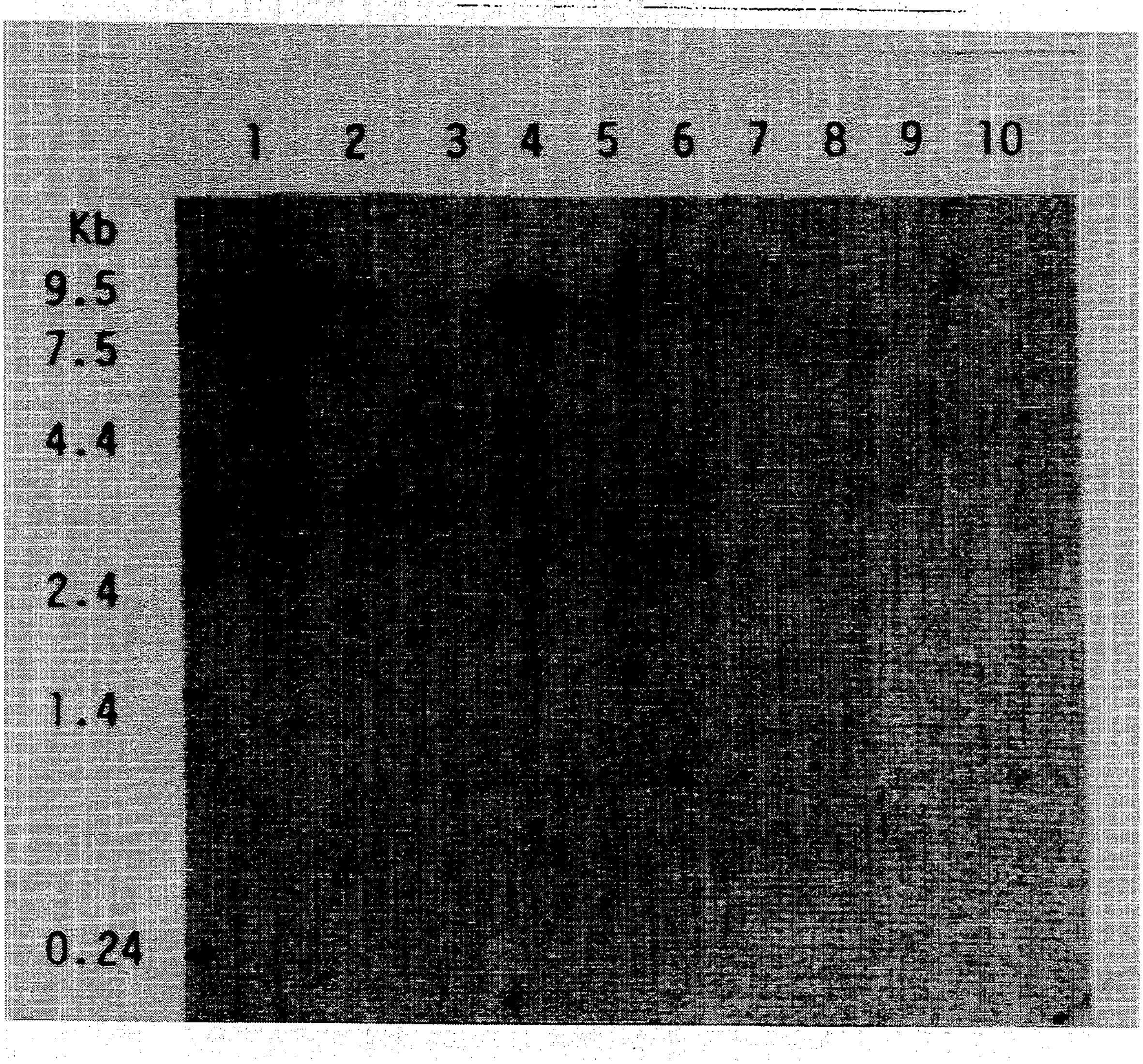

FIG. 5 shows Northern Blot analyses of RNA from cerebral tissues of the rat. In FIG. 5, the references 1 to 10 correspond respectively to:

1: hypothalamus,
2: pons-oblongata,
3: olfactory bulb,
4: olfactory tubercules,
5: striatum,
6: substantia nigra,
7: cortex,
8: hippocampus,
9: cerebellum,
10: hypophysis.

Figure 6:
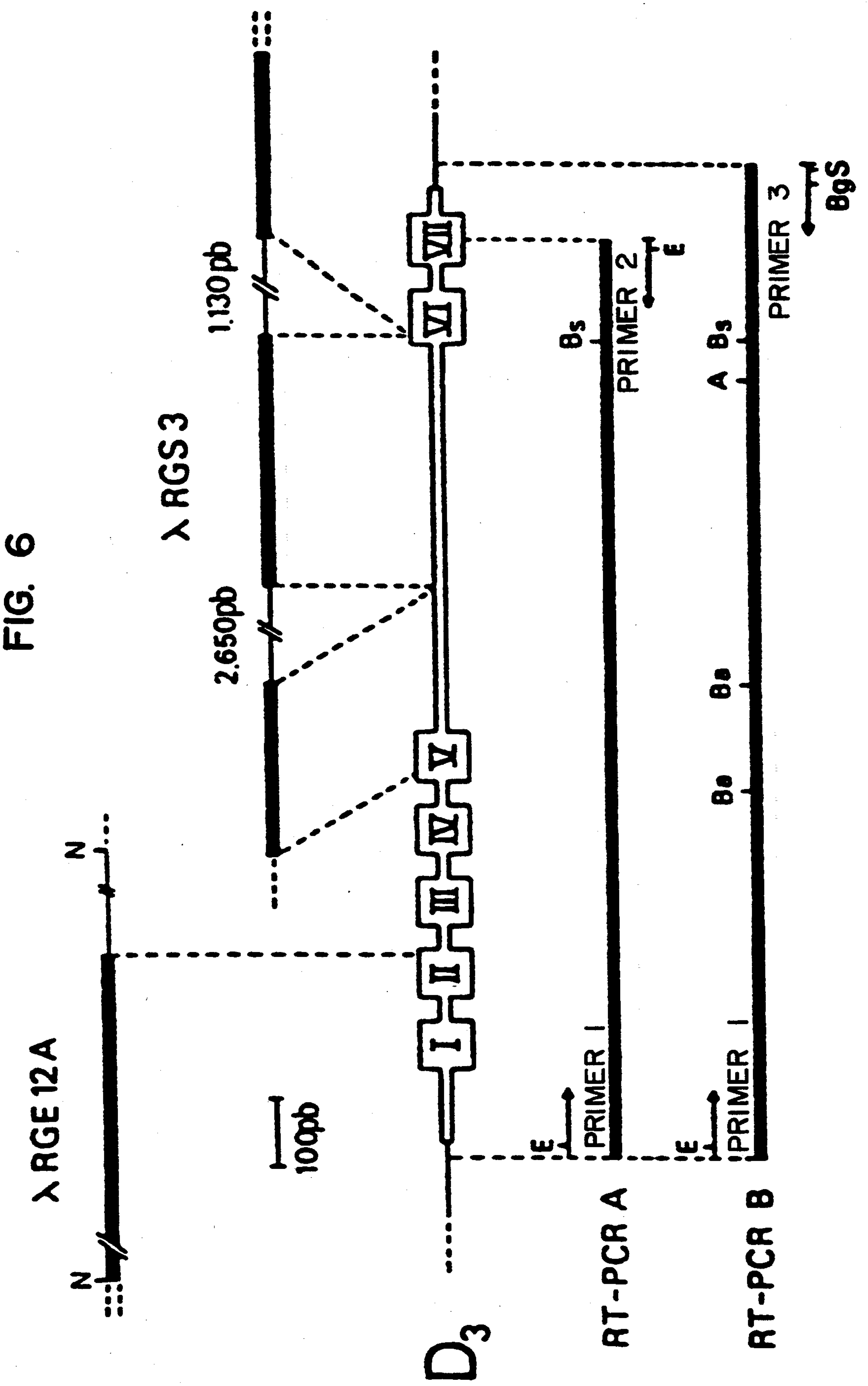

FIG. 6 is a schematic representation of the organisation of the clones obtained after screening of the genomic DNA and its amplification by the PCR technique.

The D-3 sequence is schematically shown by means of seven boxes corresponding to MbI-MbVII, the unfilled parallel lines representing the coding sequences and the single lines representing the untranslated sequences.

λRGE 12A and λRGS 3 are clones of genomic DNA, whereas RT-PCR A and B represent cDNA clones obtained by means of amplification according to the PCR technique of cDNA obtained from poly(A)+ mRNA and reverse transcriptase designated hereafter by RT-PCR. The dark lines represent the coding regions (exons of clones of genomic DNA) and the fine lines represent the introns in the clones of genomic DNA. The dotted lines indicate the continuity of the sequence. The primers 1 (SEQ ID NO:25), 2 (SEQ ID NO:26) and 3 (SEQ ID NO:27) are used for the RT-PCR technique. The restriction sites indicated are such that: A=AvaI; Ba=BamHI; Bg=BglII; Bs=Bst XI; E=EcoRI; N=NheI and S=SalI. It is to be noted that EcoRI, BglI and SalI are adaptors of the 5′ end of the primers of RT-PCR.

FIGS. 7A to D present comparisons of the properties of the D-2 and D-3 receptors expressed in the transfected CHO cells. More precisely, FIG. 7A and B show the inhibition of the binding of $^{125}$I-iodosulpride by the dopamine agonists and FIGS. 7C and D show the inhibition of the binding of $^{125}$I-iodosulpride by the dopamine antagonists.

Figure 8A:
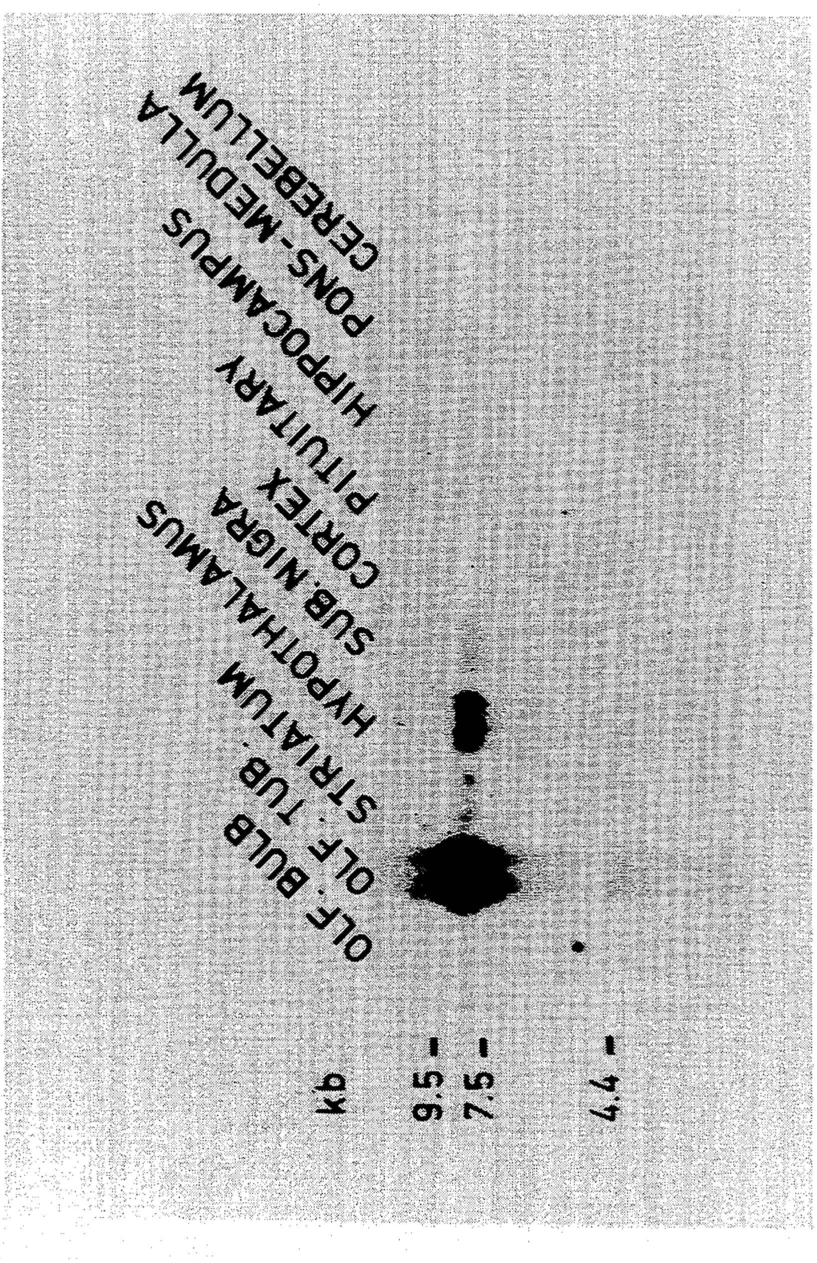
Figure 8B:
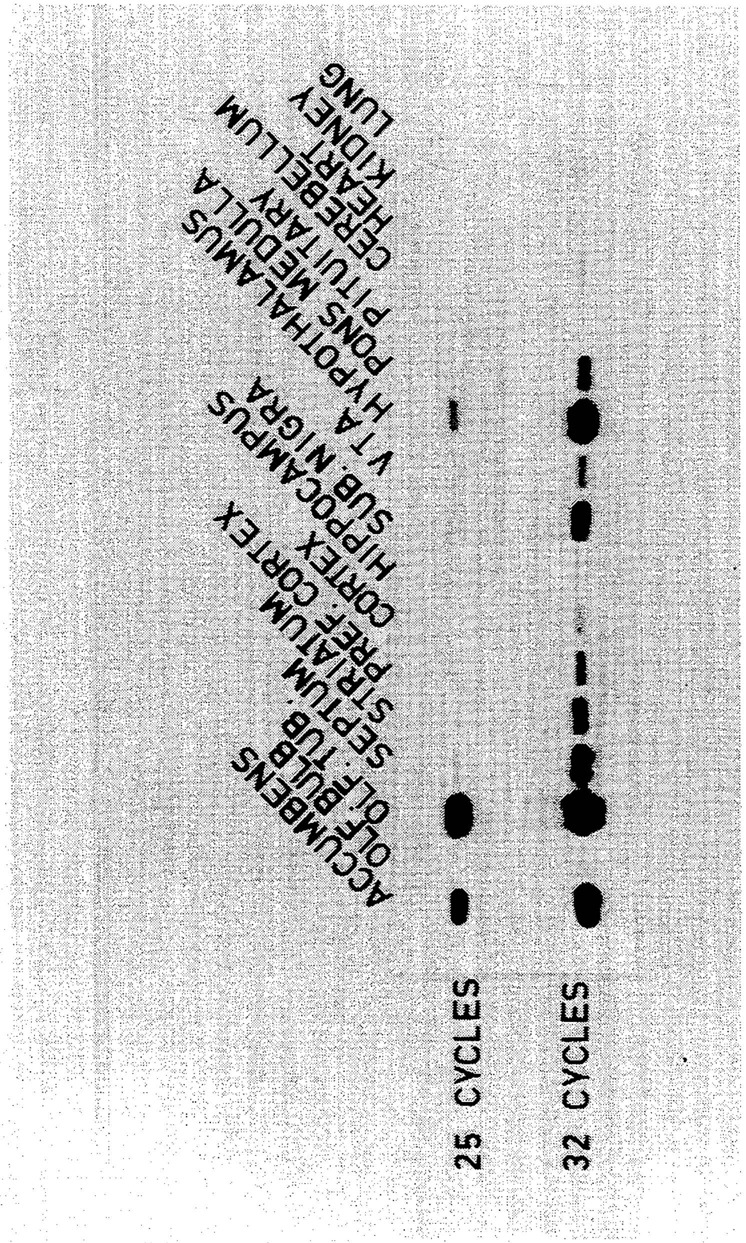
Figures 9A, 9B, 9C, 9D, 9E, 9F:
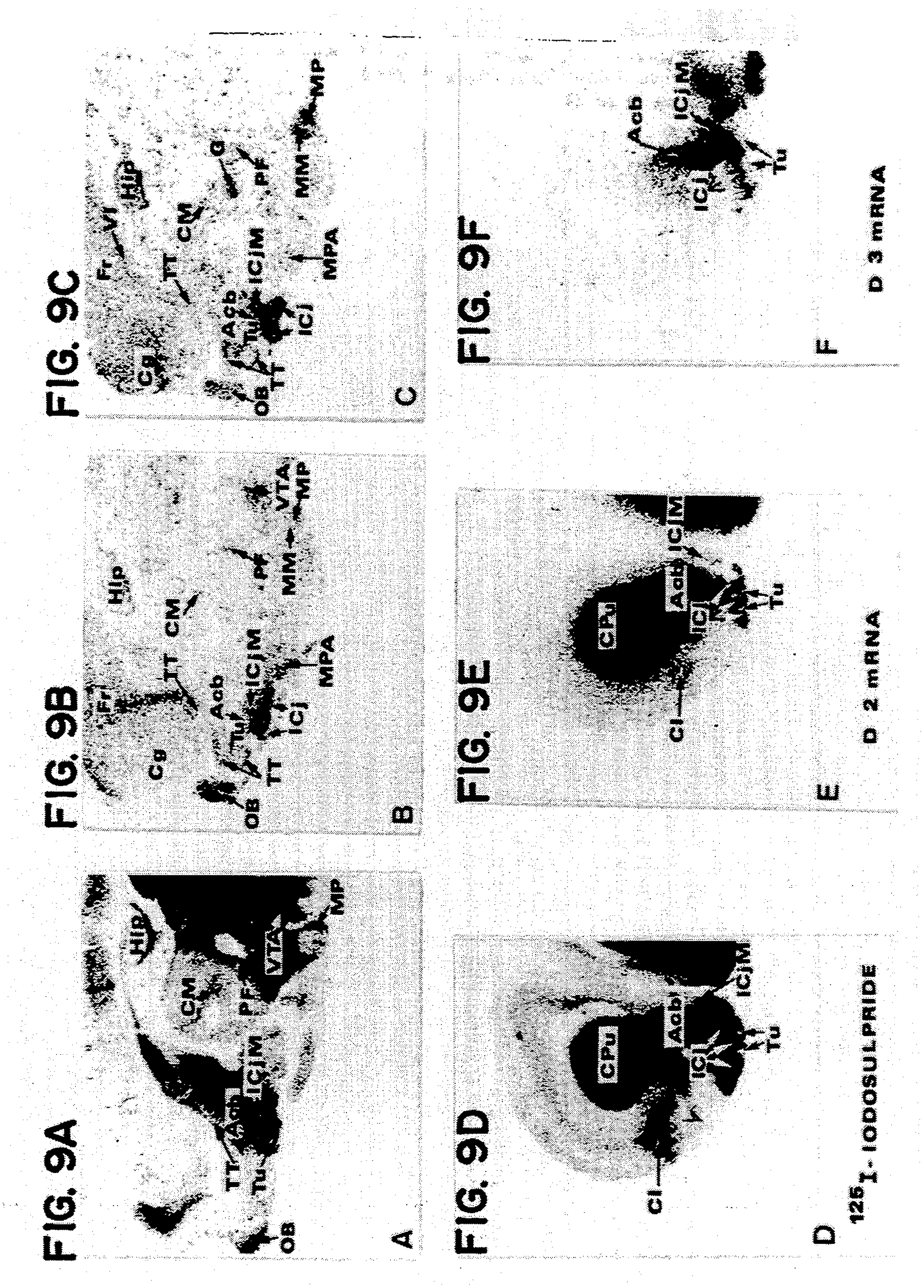

FIGS. 8A and 8B present the characterization of the transcripts of the gene for the D-3 receptor in various tissues.

FIGS. 9A to F present the autoradiographic localization of the binding sites for $^{125}$I-iodosulpride and of the messenger RNA of the D-2 or D-3 receptors in rat brain.

Figure 10:
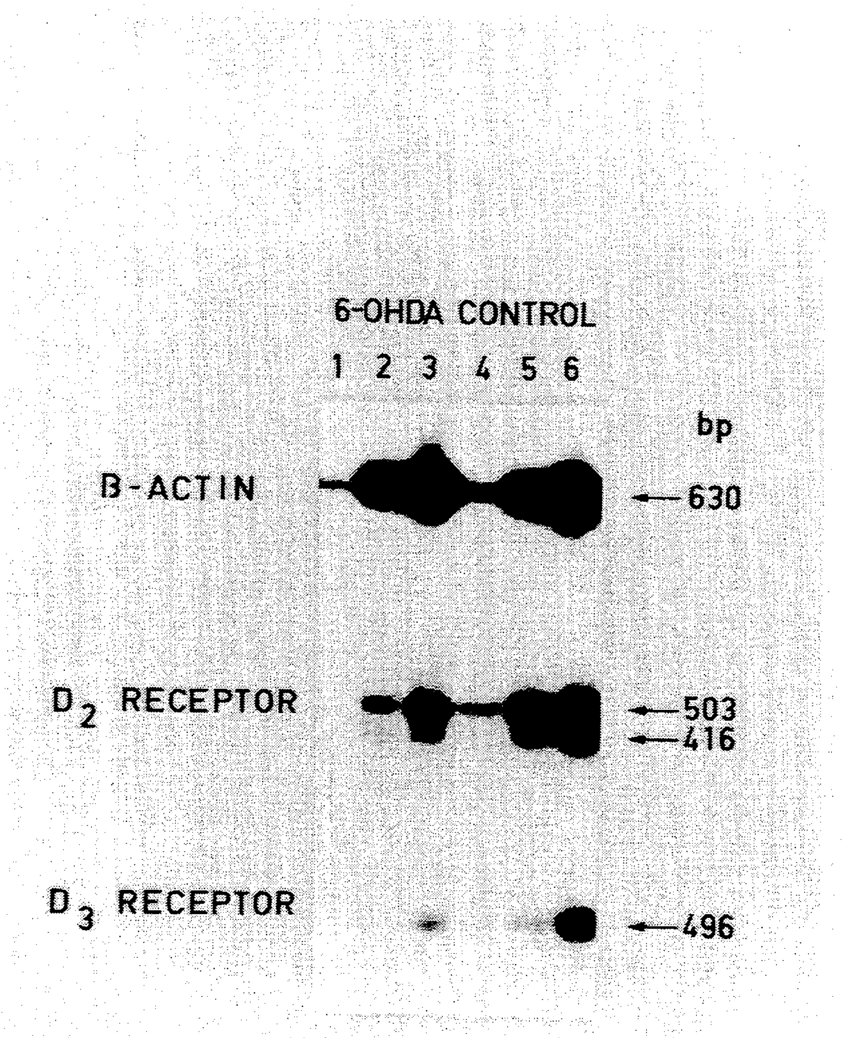

FIG. 10 presents the effects of the lesions induced by 6-hydroxydopamine on the transcripts of the genes for the D-2 and D-3 receptors in the substantia nigra.

Figure 11:
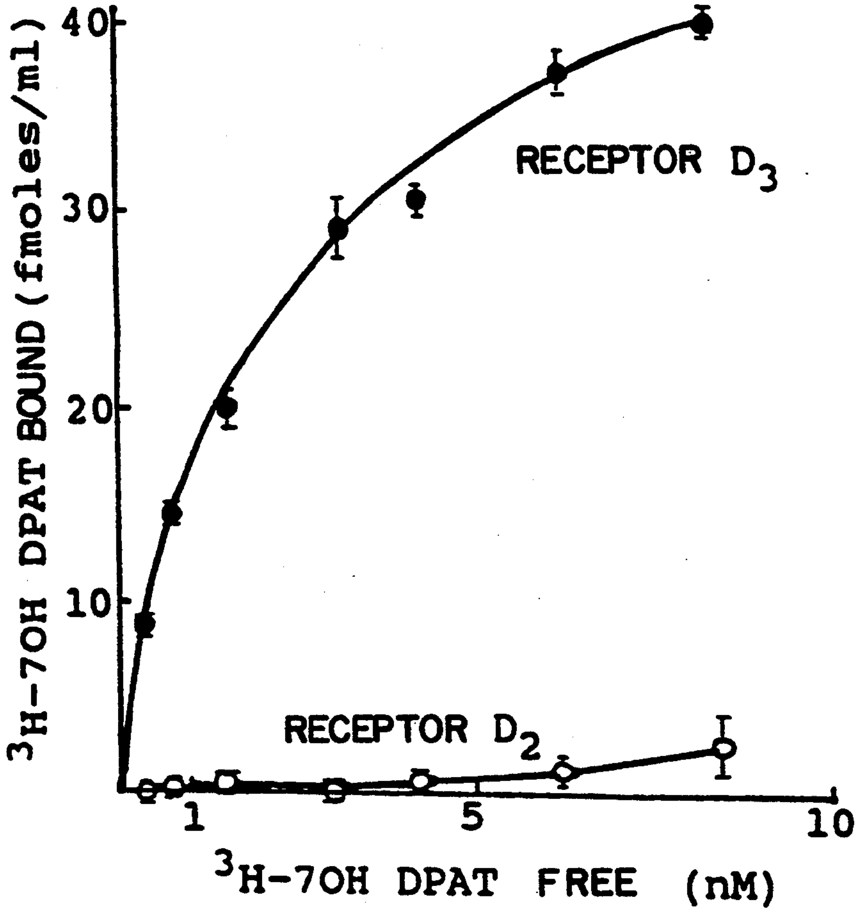

FIG. 11 presents the specific binding to the D-2 (curve with the open circles) and D-3 (curve with the filled circles) receptors in the presence of increasing concentrations of 7 OHDPAT-$^3$H. The 7 OHDPAT-$^3$H binds to membranes of cells expressing the D-3 receptor with high affinity ($K_D$—2 nM) but very slightly to those of cells expressing the D-2 receptor, which demonstrates the specificity of the ligand for the D-3 receptor.

EXAMPLES

1) Cloning of the D-3 dopaminergic receptor

Oligonucleotides derived from the D-2B dopaminergic receptor (nucleotides 146–233 according to Bunzow, J. R., Van Tol, H. H. M., Grandy, D. K., Albert, P. Salon, J., Christie, Mc. D., Machida, C. A., Neve, K. A. and Civelli, O., Nature 336, 783–787 (1988)) are radioactively labelled and used to screen a bank of cDNAs obtained from rat brain (Giros, B., Sokoloff, P., Martres, M. P., Riou, J. F., Emorine, L. J. and Schwartz, J. C. Nature 342, 923–926 (1989)). It is observed that one of the clones hybridizes weakly with a BamHI-BglII restriction fragment of the clone for the D-2A receptor but not with a Acc1—Acc1 probe (nucleotides 278–571) (SEQ ID NO:23) coding for the transmembranar regions MbII to MbV shown in FIGS.

2A and B. AatII-Msc1 of this clone, labelled with phosphorus 32 according to the technique of "nick-translation", is used to screen a genomic bank constituted from the rat, partially cut by EcoRI constructed in the vector Charon 4A. Nitrocellulose filters to which the phages were transferred are subjected to hybridization for 16 h at 42° C. in a medium containing 60% formamide, 10% dextran sulfate, 4×SSC, 8 mM Tris-HCl. pH 7.4, 1×Denhardt's, 20 μg/ml of yeast tRNA, 20 μg/ml of salmon sperm DNA, 0.1% SDS, and the probe containing $7.5\times10^5$ dpm/ml. The filters are washed twice for 20 mn at 42° C. in 2×SSC, 0.1.% SDS and twice for 20 mn in 0.2×SSC, 0.1% SDS, first at 42° C. and then at 55° C. Three identical positive clones are obtained (including λRGE 12A) out of 800,000 clones and a Nhe-1—Nhe1 fragment of 3.5 kb is subcloned into the Xbal site of M13 and sequenced (Sanger, F., Nicklen, S. and Coulson, A. R. Proc. Natl. Acad. Sci. USA, 74, 5463–5467 (1977)). Two primers derived from this sequence are synthesized (PCR-Mate 391A DNA synthesizer, Applied Biosystems) at −32 (5'-ACATTTTGGAGTCGCGTTCCTCTG, primer 4) (SEQ ID NO:24) and at −7 (CGAATTCATGGCACCTCTGAGCCAGATAAGCAC, primer 1) (SEQ ID NO:25) and a degenerated primer of the MbVII sequence of the D-2 receptor (primer 2) (SEQ ID NO:26) (5'-CGAATTCGAC(GA)GCACTGTT(GC)AC(GA)TA(GC)CC(GC)AGCCA) at 375 nM.

A single-stranded cDNA is synthesized by using the AMV reverse transcriptase (20 U, Boehringer), and poly(A)+ mRNA (2 μg) of rat brain. This matrix is amplified (Kawazaki, E. S. and Wang, P. M. In: PCR Technology (ed Erlich, H. A.) 89–97 (Stockholm Press. 1989)) by using the primer 4 (SEQ ID NO:24) and the primer 2 (SEQ ID NO:26) (75 nM of each) for 30 cycles (92° C., 52° C. and 72° C. for 1 mn each) with 2.5 U of Taq DNA polymerase (Perkin Elmer Cetus).

After resolution of the products which were obtained by the PCR technique by means of electrophoresis on agarose gel, transfer and hybridization with the probe of the AccI-AccI D-2 receptor (SEQ ID NO:23), a reactive band of 1.3 kb is excised and the DNA is extracted. This DNA is again amplified by means of the PCR technique with the primers 1 (SEQ ID NO:25) and 2 (SEQ ID NO:26). A band is detected after staining with ethidium bromide, cut, the DNA is extracted and digested with EcoRI and subcloned into M13 (clone RT-PCR A) for sequencing, and in the plasmid pGEM-4Z (Promega). A Bst XI-EcoRI restriction fragment radioactively labelled is used to screen a genomic bank constituted from the rat, partially cut by Sau 3A (Clontech) as described above. A RGS3 positive clone is obtained and analysed, and a NheI-NheI fragment of 3.5 kb which hybridizes with the Bst XI-EcoRI probe is subcloned into M13 and sequenced. A primer is synthesized 45 nucleotides downstream from the first TGA stop codon in the frame (primer 3: CCACGTCGACAGATCTCGAAGTGGGTAAAGGGAGTG) (SEQ ID NO:27). The primers 1 (SEQ ID NO:25) and 3 (SEQ ID NO:27) are then used in the RT-PCR technique as described above, using the poly(A)+ mRNA of the olfactory tubercule as source of RNA.

A band of the expected size (1.4 kb) is extracted after electrophoresis on agarose gel and digested with EcoRI-SalI for directional subcloning in M13 mp 18, M13 mp 19 and pGEM 4Z. Four individual clones in M13 are completely sequenced and prove to be identical.

2) Expression of the D-3 receptor in transfected CHO cells

Figure 7B:
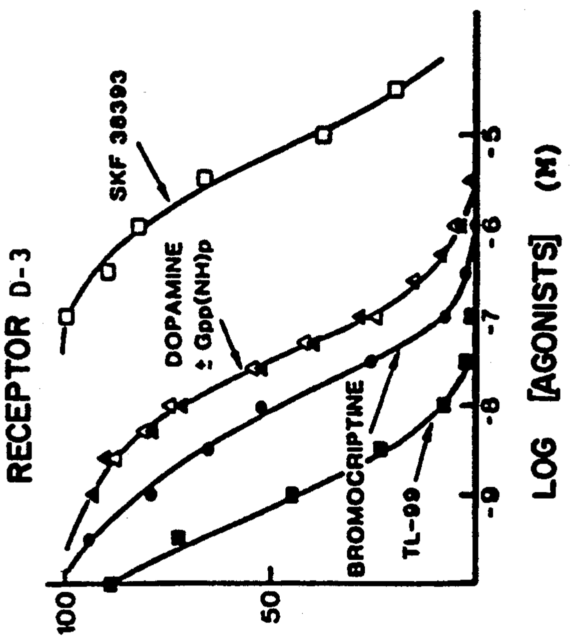
Figure 7A:
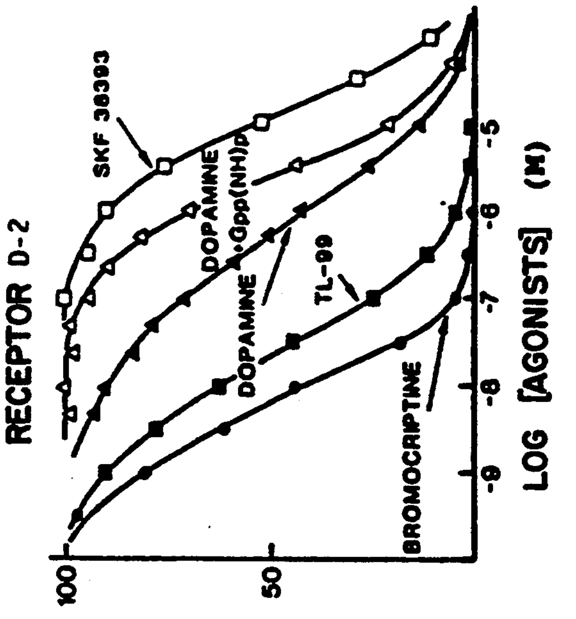
Figures 7C, 7D:
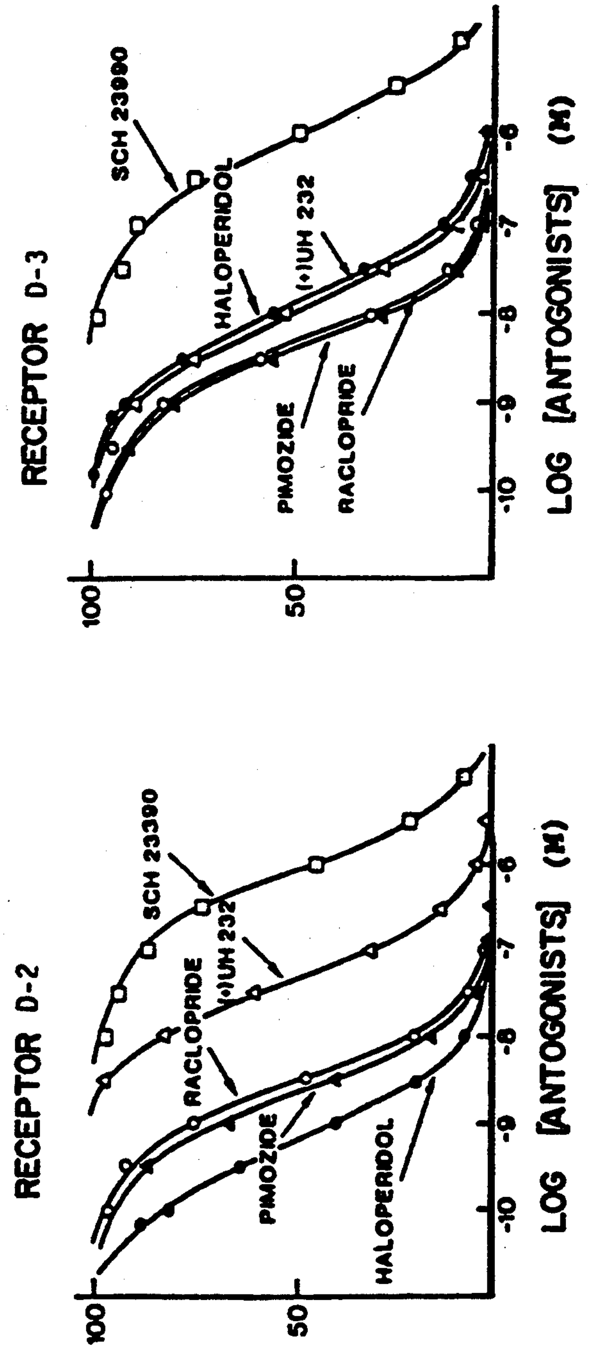

The inhibition of the $^{125}$I-iodosulpride binding was carried out using dopamine agonists (FIGS. 7A and B) and antagonists (FIGS. 7C and D).

METHOD

The expression vectors are derived from the plasmid pSV $\beta_2$-MDH (Emorine, L., Marullo, S., Delavier-Klutchko, C., Kaveri, S. V., Durieu-Trautmann, O. and Strosberg, A. D. Proc. Natl. Acad. Sci. USA 84, 6995–6999 (1987)). The $\beta_2$ adrenergic receptor is excised from pSV $\beta_2$-MDH by digestions with HindIII and EcoRI and replaced by a SmaI-EcoRI restriction fragment of the clone of the D-2A receptor by using a blunt-ended HindIII nucleotide adaptor leading to the plasmid pSV D-2. The vector needed to express the D-3 receptor is obtained by replacing the HindIII-BglII restriction fragment of pSV D-2 by a EcoRI-BglII restriction fragment of the clone RT-PCR B, by using a HindIII-EcoRI oligonucleotide adaptor leading to the plasmid pSV D-3. These constructions are cultivated and purified on a cesium chloride gradient (Sambrook J. et al., Molecular cloning—a laboratory manual. C. Nolan, ed., Cold Spring Harbor Laboratory Press, 1989) and transfected (Graham, F. L. and Van der Eb, A. J. Virology 52, 456–467 (1973)) into Chinese hamster ovary cells (CHO-K1) deficient in dihydrofolate reductase. The stable transfectants are selected in a culture medium (Dulbecco's Modified Eagle medium) not containing hypoxanthine and thymidine.

The expression of the D-3 receptor is demonstrated by the binding of $^{125}$I-iodosulpride to membranes of cells transfected according to the procedure of Martres et al. 1985. The binding experiments are performed (Martres, M. P., Bouthenet, M. L., Salés, N., Sokoloff, P. and Schwartz, J. C. Science 228, 752–755 (1985)) in a 50 mM Tris-HCl buffer (total volume 400 μl) containing 120 mM NaCl, 5 mM KCl, 2 mM $CaCl_2$, 2 mM $MgCl_2$12, 0.01% ascorbic acid, 10 μM 8-hydroxyquinoline, 0.1% of bovine serum albumin and 0.1 to 0.2 nM $^{125}$I-iodosulpride in the experiments with the D-2 and D-3 receptors, respectively.

RESULTS

The D-2 and D-3 receptors were expressed in COS-7 cells or CHO cells, which normally do not have binding sites for $^{125}$I-iodosulpride, which is a ligand exhibiting high affinity for D-2 receptors but not for the D-1 receptor in the brain. The D-2 and D-3 receptors are both labelled above a non-specific binding threshold.

In permanently transfected clones of CHO cells, the values of $K_D$ are 0.6 nM and 1.2 nM for D-2 and D-3 respectively, and the values of Bmax (Bmax representing the maximal concentration of D-2 and D-3 receptors, respectively) are about 1 pmol/mg of membrane protein in both cases.

The two receptors can be clearly distinguished by using several dopamine agonists and antagonists. The affinity of dopamine itself, in the absence of added guanyl nucleotide, is about 20 times higher for the D-3 receptor compared with that for the D-2 receptor (cf. Table 1 and FIGS. 7A and D).

In the presence of Gpp(NH)p, a guanyl nucleotide, the displacement curve for dopamine with respect to the D-2 receptor is shifted to the right (FIGS. 7A and B) indicating the presence of an appropriate G protein. On the other hand, the displacement curve for dopamine with respect to the D-3 receptor is not significantly modified in the presence of a guanyl nucleotide (FIGS. 7C and D). This may reflect the absence of an appropriate G protein in the CHO cell as well as in the COS-7 cells. This may also result from only slight modulation of dopamine binding to the D-3 receptor by the guanyl nucleotides.

Among the dopamine agonists, apomorphine and bromocriptine show similar affinities for both receptors, whereas TL99 and pergolide, considered to be presumed selective agents for the autoreceptors (Clark, D. and White, F. J. Synapse 1, 347–388 (1987); Wolf, M. E. and Roth, R. H. In: Dopamine receptors. Vol. 8 (eds Creese, I. and Fraser, C. M.) 45–96 (Alan R. Liss Inc., New-York, 1987)) and quinpirole exhibit much less affinity for the D-3 receptor than for the D-2 receptor.

Most of the dopamine antagonists belonging to various chemical classes and used clinically as neuroleptics, show affinities in the nanomolar range for the two receptors. For example, haloperidol, spiperone, thioproperazine and prochlorperazine have affinities approximately 10 to 20 times higher for the D-2 receptor than for the D-3 receptor, whereas sulpiride (−), clozapine, thioridazine, amisulpride or raclopride have affinities for the D-2 receptor only 2 to 3 times higher than those for the D-3 receptor.

The only antagonists which exhibit somewhat but significantly higher affinities for the D-3 receptor than the D-2 receptor are UH232 and AJ76 (defined below), considered to be presumed selective agents of the autoreceptors.

3) Characterization of the transcripts of the gene for the D-3 receptor in several tissues (cf. FIG. 8A and FIG. 8B):

In FIG. 8A is shown the analysis by transfer of the messenger RNAs of the D-3 receptor obtained starting from rat brain. In order to do this, poly(A)+ RNAs are prepared (Chirgwin, J. J., Przbyla, A. E., MacDonald, R. J. and Rutter, W. J. Biochemistry18, 5294–5299 (1979); Aviv, H. and Leder, P., Proc. Natl. Acad. Sci. USA 69, 1408–1412 (1972)). Samples (8 μg) are denatured, subjected to electrophoresis on agarose, transferred to nitrocellulose membranes and hybridized (Giros, B., Sokoloff, P., Martres, M. P., Riou, J. F., Emorine, L. J. and Schwartz, J. C. Nature 342, 923–926 (1989)) by using a selective BamHI-AvaI restriction fragment of 422 bp labelled with $^{32}P$ by the "nick-translation" technique to $5\times10^6$ dpm/ml; this fragment is situated in the presumed intracytoplasmic third loop. The membranes are exposed for 6 days at −80° C. with amplifying screens. The sizes of the RNA markers (in kb) are shown on the left hand side of FIG. 8A.

FIG. 8B shows the autoradiograms of the agarose gel electrophoresis of the cDNA products labelled with phosphorus 32, generated from poly(A)+ mRNAs by means of the PCR technique after amplification for 25 cycles (high) and amplification for 32 cycles (low). The single-stranded cDNA is synthesized by using 1 μg of RNA, 20 U of AMV reverse transcriptase and the primer 3 (SEQ ID NO:27) (FIGS. 2A and B). The double-stranded cDNA is synthesized and amplified by using 2.5 U of Taq polymerase, the primer 3 and an oligonucleotide corresponding to the amino acids 300–306 (FIGS. 2A and B): 5'-AAGCGCTACTACAGCATCTGC (primer 5) (SEQ ID NO:28) for 25 or 32 cycles (92° C., 56° C. and 72° C., 1 mn each). A tracer amount of ($^{32}P$)dCTP is incorporated during the amplification and the DNA is subjected to electrophoresis in a 1.5% agarose gel.

4) Autoradiographic localization of the $^{125}I$-iodosulpride binding sites and the mRNAs of the D-2 or D-3 receptors in rat brain:

This localization is presented in FIGS. 9A to 9F).

The sagittal (A,B,C) or coronal (D,E,F) sections (laterality 0.4 mm, interaural distance 10.7 mm (Paxinos, G. and Watson, C. In: The rat brain stereotaxic coordinates (Academic Press, London. 1982) are incubated either with $^{125}I$-iodosulpride (A,D), a probe for both the D-2 and the D-3 receptors, or RNA probes labelled with phosphorus 32 and selective for the mRNA of the D-2 receptor (B,E) or for the mRNA of the D-3 receptor (C,F).

The following abbreviations are used in FIGS. 9A to F: Acb: nucleus accumbens; Cl: claustrum; Cg: gyrus cinguli; CM: central median thalamic nucleus; CPu: caudate putamen; Fr: frontal cortex; G: gelatinous thalamic nucleus; Hip: hippocampal formation; Icj: islands of Calleja; ICJM: major island of Calleja; MM: median part of the median mammillary nucleus; MP: posterior part of the median mammillary nucleus; MPA: median preoptic area; OB: olfactory bulb; PF: parafascicular thalamic nucleus; Tu: olfactory tubercule; TT: tenia tecta; VTA: ventral tegmental area; VI: layer VI of the cerebral cortex.

The binding with $^{125}I$-iodosulpride is performed on unfixed cryostat sections incubated with 0.3 nM of $^{125}I$-iodosulpride, rinsed and placed in contact with a film designated by the name $^3H$-Amersham hyperfilm for 5 days (Bouthenet, M. L., Martres M. P., Sales, N. and Schwartz J. C. Neuroscience 20, 117–155 (1987)). For the in situ hybridization studies, single-stranded RNA probes labelled with $^{32}p$ are synthesized using a kit marketed under the name of Riboprobe (Promega) containing $^{32}P$-UTP and T7 RNA polymerase. The matrices (10 ng) are pGEM-4Z recombinant plasmids digested with EcoRI containing a SacI-AflII fragment of the clone of the D-2 receptor or a BamHI-AvaI fragment of the BRT-PCR clone in the correct orientation. Cryostat sections (10 μm) are mounted on plates, fixed in 4% formaldehyde, treated with proteinase K and subjected to hybridization overnight at 55° C. (Meador-Woodruff, J. H., Mansour, A., Bunzow, J. R., Van Tol, H. H. M., Watson, S. J. and Civelli, O. Proc. Natl. Acad. Sci. USA 86, 7625–7628 (1989)) with probes labelled with $2.10^6$ dpm $^{32}p$ in 50 μl. The plates are rinsed, dehydrated (Meador-Woodruff, J. H., Mansour, A., Bunzow, J. R., Van Tol, H. H. M., Watson, S. J. and Civelli, O. Proc. Natl. Acad. Sci. USA 86, 7625–7628 (1989)) and placed in contact with films designated by the name "βmax hyperfilm" (Amersham) for 20 days at −80° C.

5) Effect of the lesions induced by 6-hydroxydopamine on the transcripts of the genes for the D-2 and D-3 receptors in the substantia nigra:

The rats receive a unilateral injection of 6-hydroxydopamine (8 μg/4 μl of saline solution) in the medial bundle of the telencephalon with the coordinates A 4.7 mm, L 1.5 mm and H 1.0 mm (Paxinos, G. and Watson, C. In: The rat brain stereotaxic coordinates (Academic Press, London. 1982)). After 10 days, the rats exhibiting controlateral rotations subsequent to the administration of 0.25 mg/kg of apomorphine are selected. They are sacrificed 4 to 7 weeks after being lesioned and the total RNA of the substantia nigra or of the ventral tegmental area of each individual is prepared (Chomczynksi, P. and Sacchi, N. Analytical Biochemistry 162, 156–159 (1987)). The PCR experiments are carried out as described in relation to the FIGS. 8*a* and 8*b* by using oligonucleotides corresponding to the amino acids 43–51: 5'-GATGGTGGGTATGGGTCAGAAGGA (SEQ ID NO:29) and the amino acids 243–253: 5'-GCTCATTGCCGATAGTGATGACCT (SEQ ID NO:30) of 8-actin. In the case of the D-2 receptor, oligonucleotides are used corresponding to the amino acids 195–203: 5'-TCCGAATTCTCATTCTACGTGCCCTTCATC (SEQ ID NO:31) and the amino acids 355–363: 5'-GCTTTCTGCGGCTCATCGTCTTAA (SEQ ID NO:32). The primers (SEQ ID NO:27) 3 and 5 (SEQ ID NO:28) FIG. 8) are used in the case of the D-3 receptor.

The PCR products are obtained after 16 cycles (rows 1 and 4), 23 cycles (rows 2 and 5) and 27 cycles (rows 3 and 6) in the case of $\beta$-actin and after 23 cycles (rows 1 and 4), 27 cycles (rows 2 and 5) and 30 cycles (rows 3 and 6) in the case of the D-2 and D-3 receptors in the substantia nigra of the rat (rows 1–3: lesion side; rows 4–6: control side). The experience is repeated 4–7 times with individual tissues and parallel experiments are conducted with the ventral tegmental area. Autoradiograms of the gel are made, corresponding to 23 and 30 cycles in the case of $\beta$-actin and the receptors, respectively. The ratio of the optical densities corresponding to the receptors and to $\beta$-actin is calculated. The ratios obtained for the lesion side are then compared with the ratios obtained for the control side in each of the animals.

6) Determination of a ligand specific for the D-3 receptor:

7-hydroxy N,N'-dipropylaminotetraline radiolabelled with tritium (7 OHDPAT-$^3$H) was incubated with membranes of CHO cells expressing either the D-2 receptor or the D-3 receptor and the 7OHDPAT-$^3$H bound was separated from unbound label by filtration under vacuum.

FIG. 11 presents the specific binding to the D-2 and D-3 receptors in the presence of increasing concentrations of 7 OHDPAT-$^3$H. The 7 OHDPAT-3H is bound with high affinity ($K_D$=2 nM) to the membranes of cells expressing the D-3 receptor but only very slightly to those of cells expressing the D-2 receptor, which demonstrates the specificity of the ligand for the D-3 receptor.

It might be possible to obtain such ligands which are selective for the D-3 receptors by using the following molecules: quinpirole, pergolide, TL 99, quinerolane (described in Foreman M. M. et al., 1989, "Preclinical studies on quinerolane, a potent and highly selective D-2-dopaminergic agonist", J. Pharm. Exp. Ther., 250: 227–235) and SND 919 (described in Yamada K. et al., 1990,"Possible involvement of differing classes of dopamine D-2 receptors in yawning and stereotypy in rats", Psychopharmacology, 100: 141–144)

We claim:

1. An isolated polypeptide having dopaminergic receptor activity comprising:

a polypeptide corresponding to the sequence of 446 amino acids shown in FIGS. 1A and B (SEQ ID NO:2) or a polypeptide encoded by a nucleic acid that hybridizes to a nucleic acid probe complementary to a sequence of nucleotides extending from nucleotide 442 to 1779 in FIGS. 3A to D (SEQ ID NO:6) or FIGS. 4A to D (SEQ ID NO:7) wherein hybridization is conducted in 40–60% formamide and at 42° C.

2. The polypeptide according to claim 1, wherein said polypeptide has affinity for agonists determined by competition with the ligand $^{125}$I-iodosulpride which affinity decreases in the following order:

quinpirole > apomorphine = dopamine.

3. The polypeptide according to claim 1, wherein said polypeptide has affinity for antagonists determined by competition with the ligand $^{125}$I-iodosulpride which affinity decreases in the following order:

raclopride > UH 232 = haloperidol.

4. An isolated nucleic acid having a sequence comprising a chain of nucleotides coding for a polypeptide corresponding to claim 1.

5. An isolated nucleic acid having a sequence selected from the group consisting of a chain of nucleotides corresponding to nucleotide 1 to nucleotide 1863 of FIGS. 3A to D (SEQ ID NO:4), nucleotide 1 to nucleotide 1863 of FIGS. 4A to D (SEQ ID NO:5), nucleotide 442 to nucleotide 1779 of FIGS. 3A to D (SEQ ID NO:6), and nucleotide 442 to nucleotide 1779 of FIGS. 4A to D (SEQ ID NO:7).

6. A recombinant vector comprising a nucleic acid having a sequence according to claim 5 operably linked to transcriptional and translational regulatory control regions functional in a host, wherein the nucleic acid sequence is located at a site unessential for replication of the recombinant vector.

7. A recombinant vector according to claim 6, wherein the transcriptional regulatory control region comprises an inducible promoter, wherein the inducible promoter is operationally linked to the nucleic acid sequence and is located at a site unessential for replication of the recombinant vector.

8. A host cell transformed by a recombinant vector according to claim 6.

9. A transformed host cell according to claim 8, wherein said host cell is a bacteria.

10. A transformed host cell according to claim 8, wherein said host cell is an eukaryotic organism.

11. A nucleotide probe comprising a nucleic acid of claim 5, or a probe having a nucleotide sequence which is complementary to the nucleotide sequence of claim 5.

12. A nucleotide probe selected from the group consisting of:

a nucleotide probe corresponding to the nucleotide sequence shown in FIGS. 3A to D, extending from nucleotide at position 1 to the nucleotide at position 441 (SEQ ID NO:8);

a nucleotide probe corresponding to the nucleotide sequence shown in FIGS. 3A to D, extending from the nucleotide at position 442 to the nucleotide at position 537 (SEQ ID NO:9);

a nucleotide probe corresponding to the nucleotide sequence shown in FIGS. 3A to D, extending from the nucleotide at position 718 to the nucleotide at position 753 (SEQ ID NO:10);

a nucleotide probe corresponding to the nucleotide sequence shown in FIGS. 3A to D, extending from the nucleotide at position 820 to the nucleotide at position 888 (SEQ ID NO:11);

a nucleotide probe corresponding to the nucleotide sequence shown in FIGS. 3A to D, extending from the nucleotide at position 958 to the nucleotide at position 996 (SEQ ID NO:12);

a nucleotide probe corresponding to the nucleotide sequence shown in FIGS. 3A to D, extending from the nucleotide at position 1068 to the nucleotide at position 1240 (SEQ ID NO:13);

a nucleotide probe corresponding to the nucleotide sequence shown in FIGS. 3A to D, extending from the nucleotide at position 1068 to the nucleotide at position 1566 (SEQ ID NO:14);

a nucleotide probe corresponding to the nucleotide sequence shown in FIGS. 4A to D, extending from the nucleotide at position 820 to the nucleotide at position 888 (SEQ ID NO:15); and a probe having a nucleotide sequence which is complementary to the sequence of any said probes.

* * * * *